(12) United States Patent
Gangjee

(10) Patent No.: US 10,233,194 B2
(45) Date of Patent: Mar. 19, 2019

(54) PYRIMIDINE COMPOUNDS AND PYRIMIDO INDOLE COMPOUNDS AND METHODS OF USE

(71) Applicant: Duquesne University of the Holy Spirit, Pittsburgh, PA (US)

(72) Inventor: Aleem Gangjee, Allison Park, PA (US)

(73) Assignee: Duquesne Unversity of the Holy Spirit, Pittsburgh, PA (US)

( * ) Notice: Subject to any disclaimer, the term of this patent is extended or adjusted under 35 U.S.C. 154(b) by 0 days.

(21) Appl. No.: 15/479,752

(22) Filed: Apr. 5, 2017

(65) Prior Publication Data

US 2017/0253612 A1    Sep. 7, 2017

Related U.S. Application Data

(62) Division of application No. 14/820,725, filed on Aug. 7, 2015, now Pat. No. 9,688,690.

(60) Provisional application No. 62/035,234, filed on Aug. 8, 2014.

(51) Int. Cl.
| | |
|---|---|
| *C07D 487/04* | (2006.01) |
| *C07D 495/04* | (2006.01) |
| *A61K 31/343* | (2006.01) |
| *C07D 403/02* | (2006.01) |
| *A61K 31/505* | (2006.01) |
| *C07D 405/02* | (2006.01) |
| *A61K 31/4709* | (2006.01) |
| *C07D 239/48* | (2006.01) |

(52) U.S. Cl.
CPC .......... *C07D 495/04* (2013.01); *A61K 31/343* (2013.01); *A61K 31/4709* (2013.01); *A61K 31/505* (2013.01); *C07D 239/48* (2013.01); *C07D 403/02* (2013.01); *C07D 405/02* (2013.01); *C07D 487/04* (2013.01)

(58) Field of Classification Search
CPC ........................... C07D 487/04; A61K 31/519
USPC ........................................ 544/280; 514/265.1
See application file for complete search history.

(56) References Cited

U.S. PATENT DOCUMENTS

| | | | | |
|---|---|---|---|---|
| 8,946,239 B2 * | 2/2015 | Gangjee | ............... | C07D 239/70 514/260.1 |
| 2009/0280133 A1 | 11/2009 | Suzuki et al. | | |
| 2010/0010016 A1 | 1/2010 | Gangjee | | |
| 2010/0227858 A1 | 9/2010 | Finlay et al. | | |
| 2011/0207757 A1 | 8/2011 | Gangjee | | |
| 2012/0264768 A1 | 10/2012 | Gangjee | | |
| 2014/0066448 A1 | 3/2014 | Combs et al. | | |

FOREIGN PATENT DOCUMENTS

WO    2009144632 A1    12/2009

OTHER PUBLICATIONS

Gangjee et al., Design, Synthesis, and Biological Evaluation of 2,4-Diamino-5-methyl-6-substituted-pyrrolo[2,3-d]pyrimidines as Dihydrofolate Reductase Inhibitors, J. Med. Chem. 47(14), pp. 3689-3692 (2004).*

Bangjee, A. et al., Design and Synthesis of Classical and Nonclassical 6-Arylthio-2,4-diamino-5-ethylpyrrolo[2,3-d] pyrimidines as Antifolates, J. Med. Chem, 2007, 3046-3053, vol. 50, American Chemical Society.

International Search Report and Written Opinion dated Nov. 20, 2015 for PCT/US15/44159 filed Aug. 7, 2015.

* cited by examiner

*Primary Examiner* — Deepak R Rao
(74) *Attorney, Agent, or Firm* — Buchanan Ingersoll & Rooney PC; Craig G. Cochenour, Esq.

(57) ABSTRACT

The present invention discloses a compound comprising the formula:

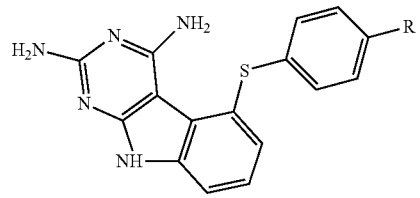

wherein R is hydrogen or an alkyl group having from one to ten carbon atoms, or a compound of the formula wherein the S is replaced by $CH_2$, and optionally comprising a pharmaceutically acceptable salt, hydrate, or solvate thereof. A method of treating a patient having cancer or a disease comprising administering to a patient an effective amount of the compound or pharmaceutically acceptable salt, hydrate, or solvate thereof.

2 Claims, 4 Drawing Sheets

PYRIMIDINE COMPOUNDS AND PYRIMIDO INDOLE COMPOUNDS AND METHODS OF USE

CROSS-REFERENCE TO RELATED APPLICATION

This divisional patent application claims the benefit of pending U.S. patent application Ser. No. 14/820,725, filed on Aug. 7, 2015, which claims the benefit of U.S. Provisional Patent Application Ser. No. 62/035,234, filed Aug. 8, 2014. The entire contents of U.S. patent application Ser. Nos. 14/820,725 and 62/035,234 are incorporated by reference into this divisional patent application as if fully written herein.

STATEMENT REGARDING FEDERALLY SPONSORED RESEARCH

This invention was made with government support under grant numbers RO1CA142868, CA136944, CA125153, and CA152316 awarded by the National Institutes of Health, National Cancer Institute, and under grant number RO1AI098458 awarded by the National Institutes of Health, National Institute of Allergy and Infectious Diseases. The government has certain rights in the invention.

BACKGROUND OF THE INVENTION

1. Field of the Invention

This invention provides substituted pyrimidine compounds and pyrimido indole compounds that are useful in treating a patient having cancer. The compounds of this invention are useful as anti-tubulin agents, as dihydrofolate reductase inhibitors, and as single agent combination chemotherapeutic agents inhibiting VEGFR-2, PDGFR-β, and human thymidylate synthase (hTS).

2. Description of the Background Art

Microtubules are ever-changing, dynamic, filamentous polymers which make up one component of the cytoskeleton. FIG. 1 shows representative known microtubule binding anti-tubulin agents. They are composed of α-tubulin and β-tubulin heterodimers, which polymerize to form long, slender microtubule polymers. Amongst many other functions, they are involved in maintaining cell shape, cell signaling and are involved in cell division. During mitosis the dynamics of microtubules are critical to normal function of the mitotic spindle. During the interphase the rate of microtubule turnover is 4- to 100-fold slower than that at the anaphase.[1] After the formation of the mitotic spindle, the actions of microtubules help partition the chromosomes into the two different daughter cells. Failure of normal microtubule dynamics can lead to mitotic arrest and subsequent cell death.[1]

Microtubule binding agents are the most widely used agents utilized in cancer chemotherapy.[1-3] FIG. 1 shows representative known microtubule binding anti-tubulin agents. Based on the site of binding on microtubules (see FIG. 2), these agents are classified as Vinca site binding agents, paclitaxel site binding agents or colchicine site binding agents.[1-3] Expression of the β-III tubulin isotype is one of the main reasons for the clinical resistance developed towards the use of vinorelbine as well as taxanes in a range of solid tumors including lung, ovarian, breast and gastric. In addition, these agents act as substrates for P-glycoprotein (P-gp), thereby, rendering them less effective against tumors that express P-gp due to low intracellular accumulation.[1-3]

SUMMARY OF THE INVENTION

A method of treating a patient is provided having a disease comprising administering to a patient an effective amount of one or more of the compounds of this invention. The method includes administering an effective amount of a salt, hydrate, or solvate of at least one of the compound(s) of this invention to the patient.

In one embodiment of this invention, a compound is provided comprising the formula:

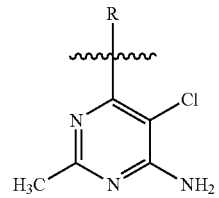

wherein R is selected from one of the following groups consisting of:

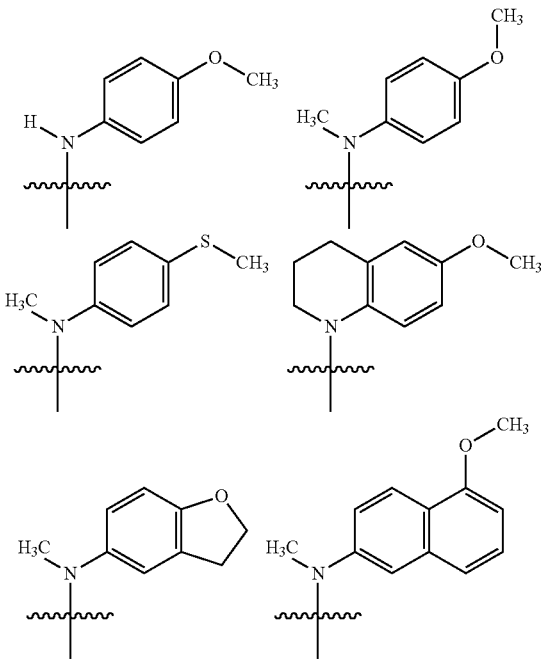

and optionally comprising a pharmaceutically acceptable salt or hydrate thereof.

In another embodiment of this invention, a compound is provided comprising the formula:

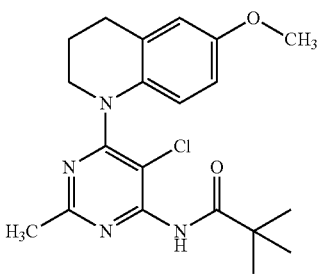

and optionally comprising a pharmaceutically acceptable salt or hydrate thereof.

In another embodiment of this invention, a compound is provided comprising the formula:

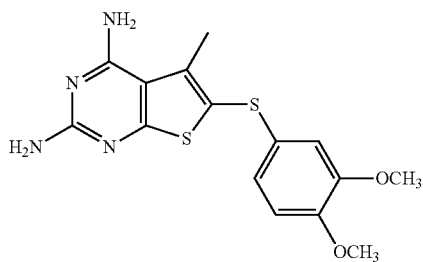 [SMILES: COc1ccc(Sc2sc3nc(N)nc(N)c3c2C)cc1OC]

and optionally comprising a pharmaceutically acceptable salt or hydrate thereof.

In another embodiment of this invention, a compound is provided comprising the formula:

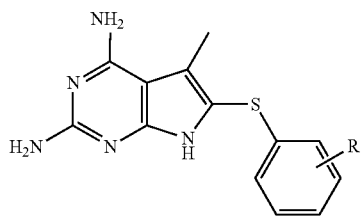

wherein R is 2-$OCH_3$, 3-$OCH_3$, 4-$OCH_3$, or 3,4-di$OCH_3$, and optionally comprising a pharmaceutically acceptable salt or hydrate thereof.

In another embodiment of this invention, a compound is provided comprising the formula:

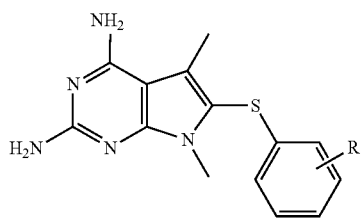

wherein R is 2-$OCH_3$, 3-$OCH_3$, 4-$OCH_3$, or 3,4-di$OCH_3$, and optionally comprising a pharmaceutically acceptable salt or hydrate thereof.

In another embodiment of this invention, a compound is provided comprising the formula:

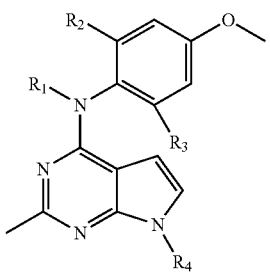

wherein $R_1$ is hydrogen or an alkyl group having from one to ten carbon atoms, $R_2$ is hydrogen or an alkyl group having from one to ten carbon atoms, $R_3$ is hydrogen or an alkyl group having from one to ten carbon atoms, and $R_4$ is hydrogen or an alkyl group having from one to ten carbon atoms, wherein $R_1$, $R_2$, $R_3$, and $R_4$ are independently selected and may be the same or different, and optionally comprising a pharmaceutically acceptable salt or hydrate thereof.

In another embodiment of this invention, a compound is provided comprising the formula:

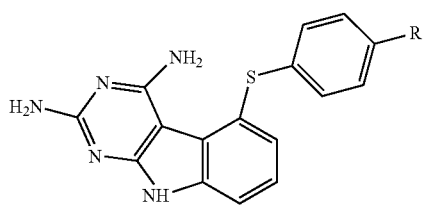

wherein R is hydrogen or an alkyl group having from one to ten carbon atoms, and optionally comprising a pharmaceutically acceptable salt or hydrate thereof.

In another embodiment of this invention, a compound is provided comprising the formula:

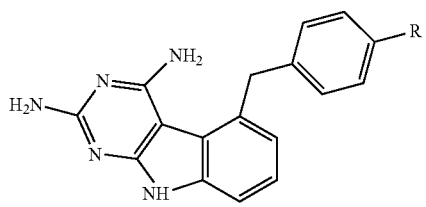

wherein R is hydrogen or an alkyl group having from one to ten carbon atoms, and optionally comprising a pharmaceutically acceptable salt or hydrate thereof.

In another embodiment of this invention, a compound is provided comprising the formula:

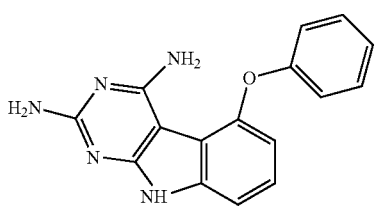 [SMILES: Nc1nc(N)c2c(n1)[nH]c1cccc(Oc3ccccc3)c12]

and optionally comprising a pharmaceutically acceptable salt or hydrate thereof.

In another embodiment of this invention, a compound is provided comprising the

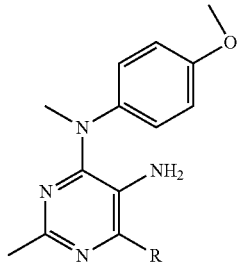

formula:
wherein R is hydrogen, an alkyl group having from one to ten carbon atoms, $NH_2$, I, or CN, and optionally comprising a pharmaceutically acceptable salt or hydrate thereof.

In yet another embodiment of this invention, a pharmaceutical composition is provided comprising a therapeutically effective amount of a compound of the formula:

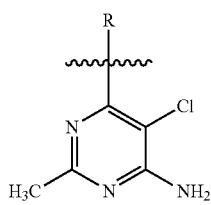

wherein R is selected from one of the following groups consisting of:

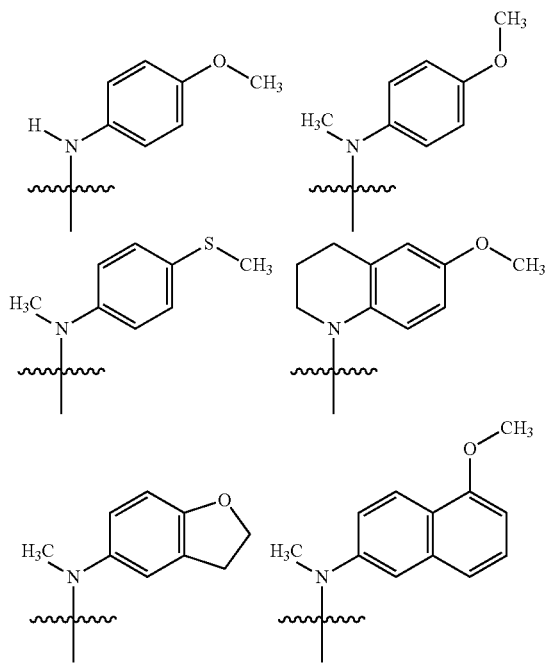

and optionally comprising a pharmaceutically acceptable salt or hydrate thereof.

In another embodiment of this invention, a pharmaceutical composition is provided comprising a therapeutically effective amount of a compound of the formula:

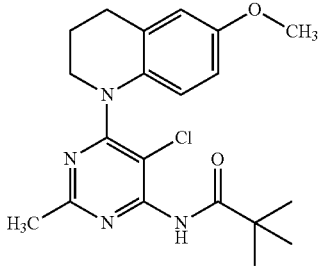

and optionally comprising a pharmaceutically acceptable salt or hydrate thereof.

In another embodiment of this invention, a pharmaceutical composition is provided comprising a therapeutically effective amount of a compound of the formula:

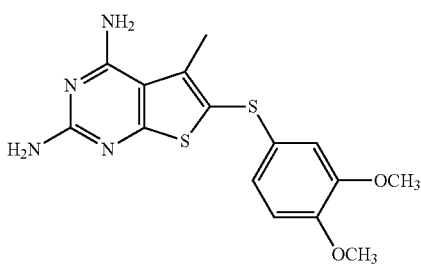

and optionally comprising a pharmaceutically acceptable salt or hydrate thereof.

In another embodiment of this invention, a pharmaceutical composition is provided comprising a therapeutically effective amount of a compound of the formula:

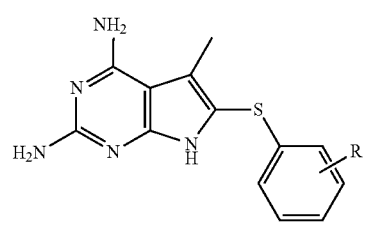

wherein R is 2-$OCH_3$, 3-$OCH_3$, 4-$OCH_3$, or 3,4-di$OCH_3$, and optionally comprising a pharmaceutically acceptable salt or hydrate thereof.

In another embodiment of this invention, a pharmaceutical composition is provided comprising a therapeutically effective amount of a compound of the formula:

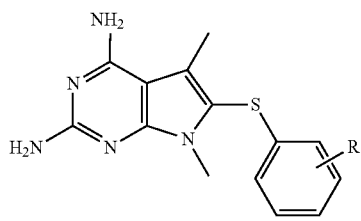

wherein R is 2-OCH$_3$, 3-OCH$_3$, 4-OCH$_3$, or 3,4-diOCH$_3$, and optionally comprising a pharmaceutically acceptable salt or hydrate thereof.

In another embodiment of this invention, a pharmaceutical composition is provided comprising a therapeutically effective amount of a compound of the formula:

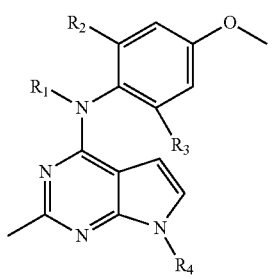

wherein $R_1$ is hydrogen or an alkyl group having from one to ten carbon atoms, $R_2$ is hydrogen or an alkyl group having from one to ten carbon atoms, $R_3$ is hydrogen or an alkyl group having from one to ten carbon atoms, and $R_4$ is hydrogen or an alkyl group having from one to ten carbon atoms, wherein $R_1$, $R_2$, $R_3$, and $R_4$ are independently selected and may be the same or different, and optionally comprising a pharmaceutically acceptable salt or hydrate thereof.

In another embodiment of this invention, a pharmaceutical composition is provided comprising a therapeutically effective amount of a compound of the formula:

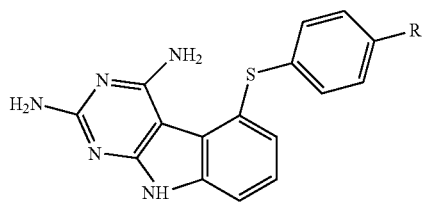

wherein R is hydrogen or an alkyl group having from one to ten carbon atoms, and optionally comprising a pharmaceutically acceptable salt or hydrate thereof.

In another embodiment of this invention, a pharmaceutical composition is provided comprising a therapeutically effective amount of a compound of the formula:

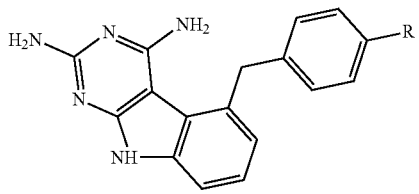

wherein R is hydrogen or an alkyl group having from one to ten carbon atoms, and optionally comprising a pharmaceutically acceptable salt or hydrate thereof.

In another embodiment of this invention, a pharmaceutical composition is provided comprising a therapeutically effective amount of a compound of the formula:

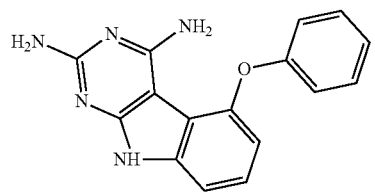 [SMILES: Nc1nc(N)c2c(n1)[nH]c1cccc(Oc3ccccc3)c12]

and optionally comprising a pharmaceutically acceptable salt or hydrate thereof.

In another embodiment of this invention, a pharmaceutical composition is provided comprising a therapeutically effective amount of a compound of the formula:

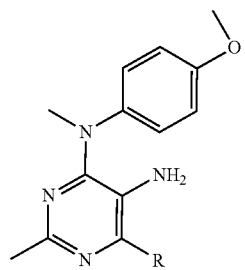

wherein R is hydrogen, an alkyl group having from one to ten carbon atoms, NH$_2$, I, or CN, and optionally comprising a pharmaceutically acceptable salt or hydrate thereof.

In yet another embodiment of this invention, a method of treating a patient having cancer or a disease is provided comprising administering to a patient an effective amount of a compound comprising formula:

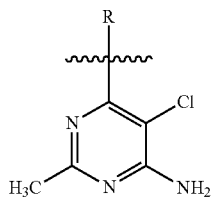

wherein R is selected from one of the following groups consisting of:

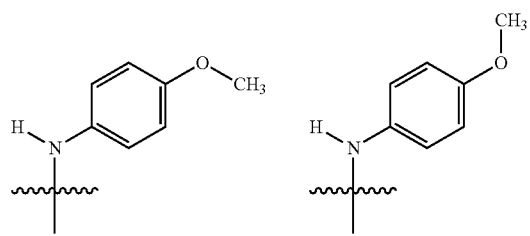
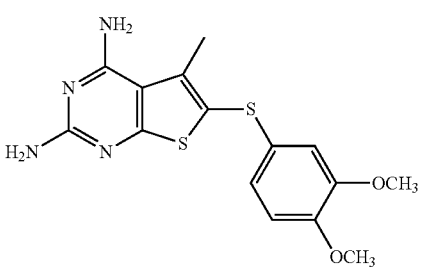 [SMILES: COc1ccc(Sc2sc3nc(N)nc(N)c3c2C)cc1OC]

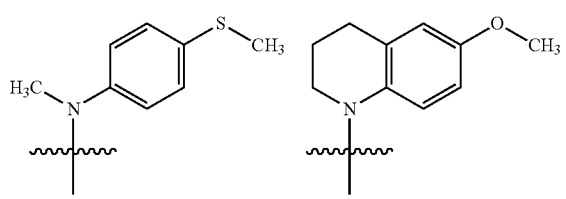

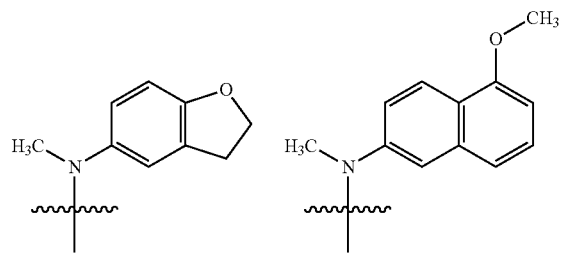

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

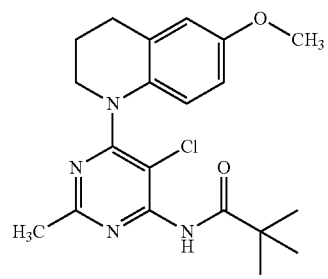

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

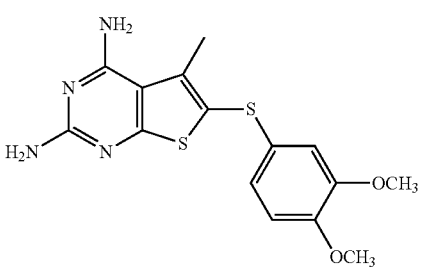 [SMILES: COc1ccc(Sc2sc3nc(N)nc(N)c3c2C)cc1OC]

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

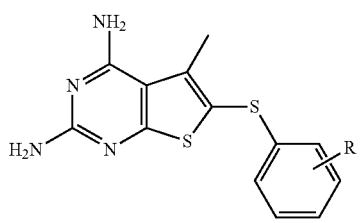

wherein R is 2-OCH$_3$, 3-OCH$_3$, 4-OCH$_3$, or 3,4-diOCH$_3$, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

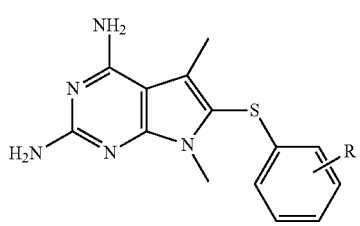

wherein R is 2-OCH$_3$, 3-OCH$_3$, 4-OCH$_3$, or 3,4-diOCH$_3$, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

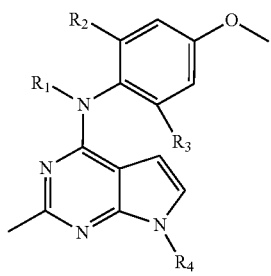

wherein $R_1$ is hydrogen or an alkyl group having from one to ten carbon atoms, $R_2$ is hydrogen or an alkyl group having from one to ten carbon atoms, $R_3$ is hydrogen or an alkyl group having from one to ten carbon atoms, and $R_4$ is hydrogen or an alkyl group having from one to ten carbon atoms, wherein $R_1$, $R_2$, $R_3$, and $R_4$ are independently selected and may be the same or different, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

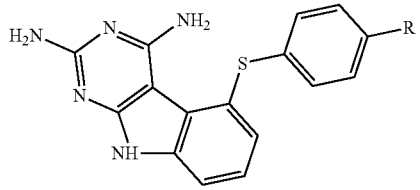

wherein R is hydrogen or an alkyl group having from one to ten carbon atoms, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

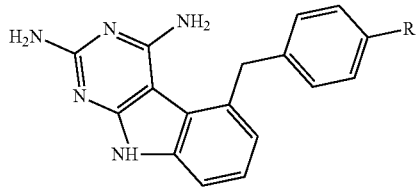

wherein R is hydrogen or an alkyl group having from one to ten carbon atoms, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

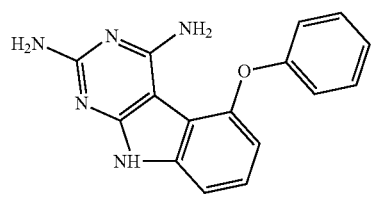 [SMILES: Nc1nc(N)c2c(n1)[nH]c1cccc(Oc3ccccc3)c12]

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

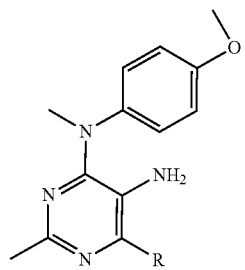

wherein R is hydrogen, an alkyl group having from one to ten carbon atoms, $NH_2$, I, or CN, and optionally comprising a pharmaceutically acceptable salt or hydrate or solvate thereof, and including administering an effective amount of said salt, hydrate, or solvate of said compound to said patient.

DETAILED DESCRIPTION OF THE INVENTION

Figure 1:
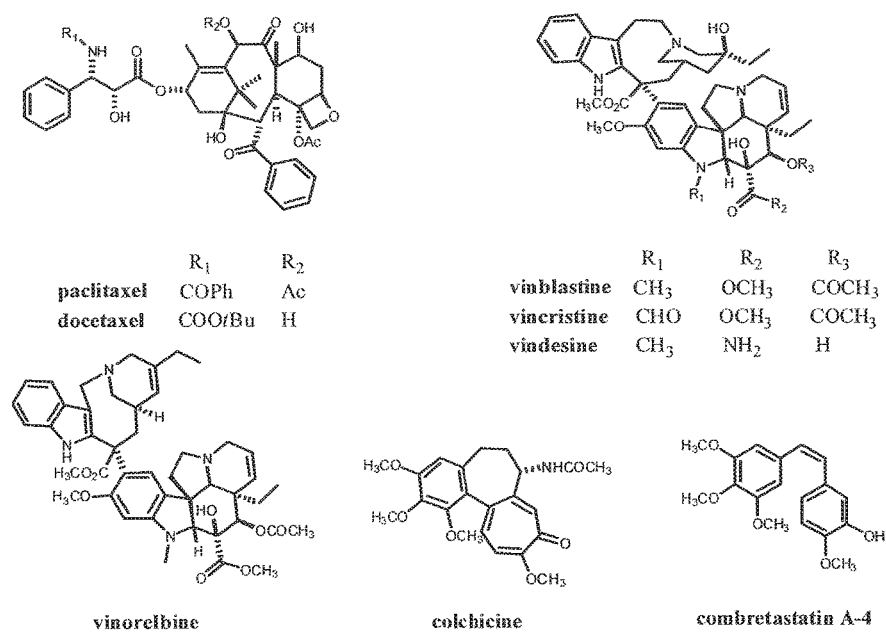
FIG. 1 shows the structures of known microtubule binding anti-tubulin agents.
Figure 2:
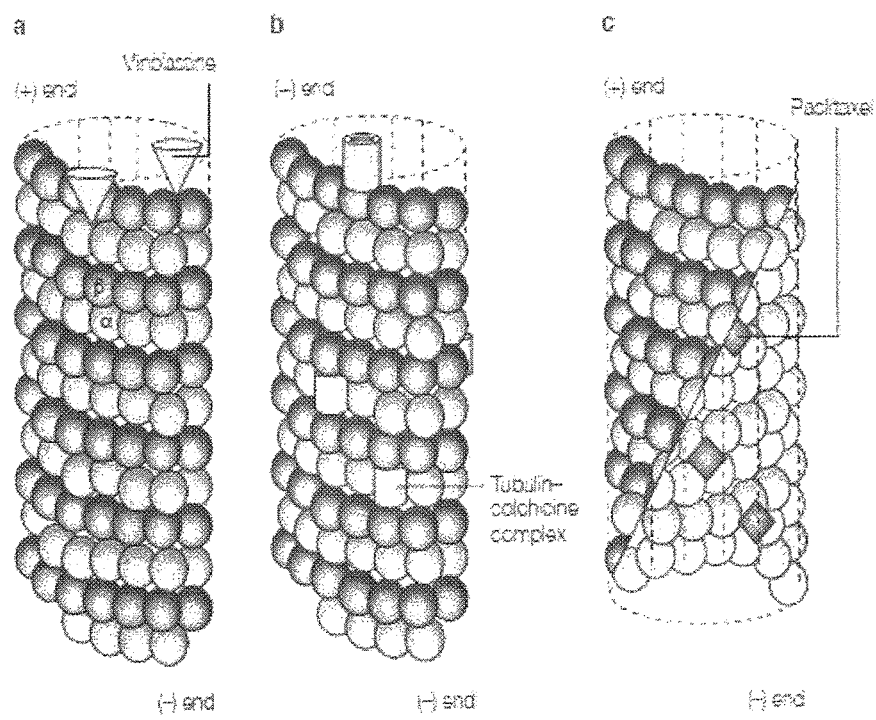
FIG. 2 shows different binding sites on microtubules.

The present invention provides substituted pyrimidine compounds and pyrimido indole compounds that are useful in treating a patient having cancer. The compounds of this invention are useful as anti-tubulin agents, as dihydrofolate reductase inhibitors, and as single agent combination chemotherapeutic agents inhibiting VEGFR-2, PDGFR-β, and human thymidylate synthase (hTS), respectively.

In one embodiment of this invention, a compound is provided comprising the formula:

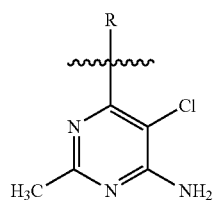

wherein R is selected from one of the following groups consisting of:

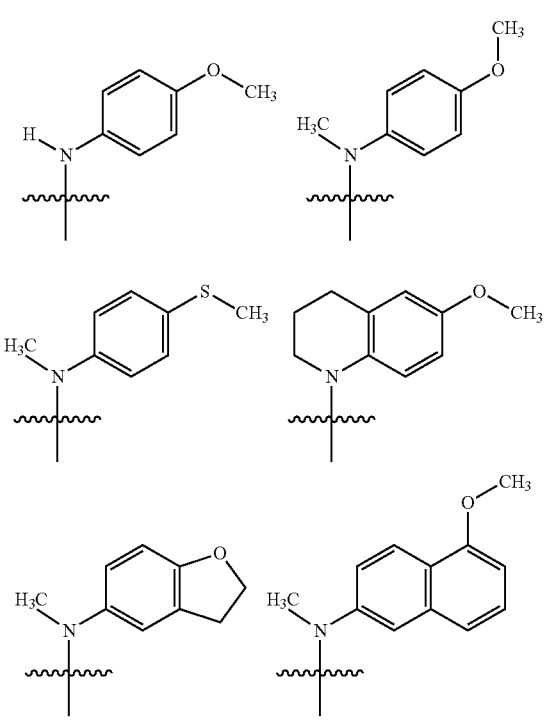

and optionally comprising a pharmaceutically acceptable salt or hydrate thereof.

In another embodiment of this invention, a compound is provided comprising the formula:

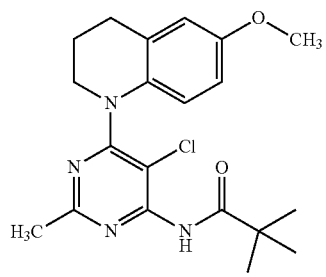

and optionally comprising a pharmaceutically acceptable salt or hydrate thereof.

In another embodiment of this invention, a compound is provided comprising the formula:

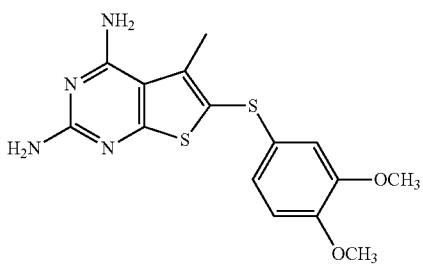

and optionally comprising a pharmaceutically acceptable salt or hydrate thereof.

In another embodiment of this invention, a compound is provided comprising the formula:

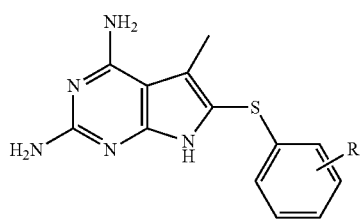

wherein R is 2-OCH$_3$, 3-OCH$_3$, 4-OCH$_3$, or 3,4-diOCH$_3$, and optionally comprising a pharmaceutically acceptable salt or hydrate thereof.

In another embodiment of this invention, a compound is provided comprising the formula:

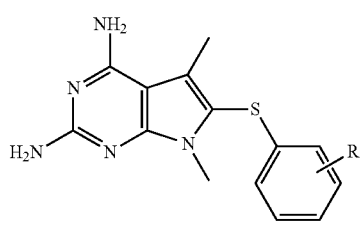

wherein R is 2-OCH$_3$, 3-OCH$_3$, 4-OCH$_3$, or 3,4-diOCH$_3$, and optionally comprising a pharmaceutically acceptable salt or hydrate thereof.

In another embodiment of this invention, a compound is provided comprising the formula:

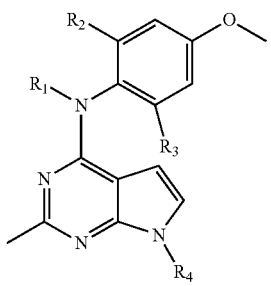

wherein $R_1$ is hydrogen or an alkyl group having from one to ten carbon atoms, $R_2$ is hydrogen or an alkyl group having from one to ten carbon atoms, $R_3$ is hydrogen or an alkyl group having from one to ten carbon atoms, and $R_4$ is hydrogen or an alkyl group having from one to ten carbon atoms, wherein $R_1$, $R_2$, $R_3$, and $R_4$ are independently selected and may be the same or different, and optionally comprising a pharmaceutically acceptable salt or hydrate thereof.

In another embodiment of this invention, a compound is provided comprising the formula:

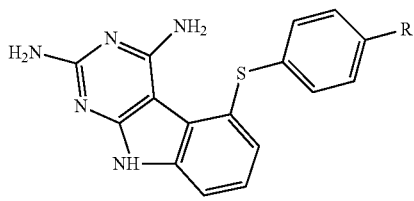

wherein R is hydrogen or an alkyl group having from one to ten carbon atoms, and optionally comprising a pharmaceutically acceptable salt or hydrate thereof.

In another embodiment of this invention, a compound is provided comprising the formula:

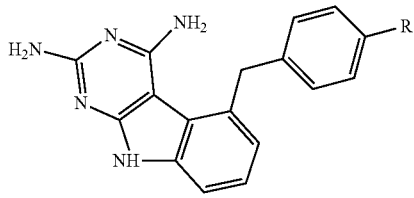

wherein R is hydrogen or an alkyl group having from one to ten carbon atoms, and optionally comprising a pharmaceutically acceptable salt or hydrate thereof.

In another embodiment of this invention, a compound is provided comprising the formula:

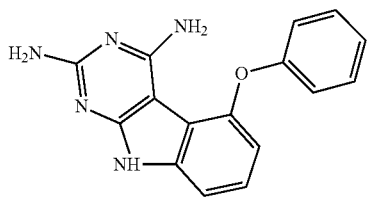 [SMILES: Nc1nc(N)c2c(n1)[nH]c1cccc(Oc3ccccc3)c12]

and optionally comprising a pharmaceutically acceptable salt or hydrate thereof.

In another embodiment of this invention, a compound is provided comprising the formula:

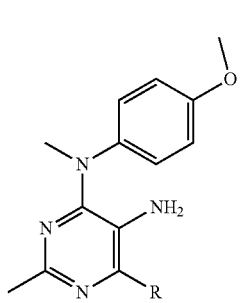

wherein R is hydrogen, an alkyl group having from one to ten carbon atoms, $NH_2$, I, or CN, and optionally comprising a pharmaceutically acceptable salt or hydrate thereof.

In yet another embodiment of this invention, a pharmaceutical composition is provided comprising a therapeutically effective amount of a compound of the formula:

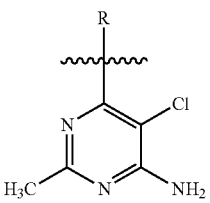

wherein R is selected from one of the following groups consisting of:

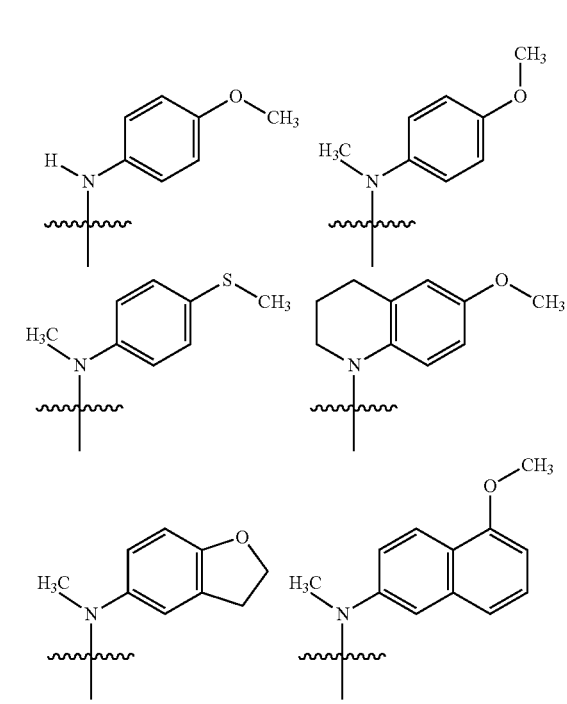

and optionally comprising a pharmaceutically acceptable salt or hydrate thereof.

In another embodiment of this invention, a pharmaceutical composition is provided comprising a therapeutically effective amount of a compound of the formula:

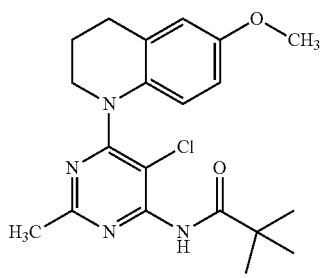 [SMILES: COc1ccc2c(c1)CCCN2c1nc(C)nc(NC(=O)C(C)(C)C)c1Cl]

and optionally comprising a pharmaceutically acceptable salt or hydrate thereof.

In another embodiment of this invention, a pharmaceutical composition is provided comprising a therapeutically effective amount of a compound of the formula:

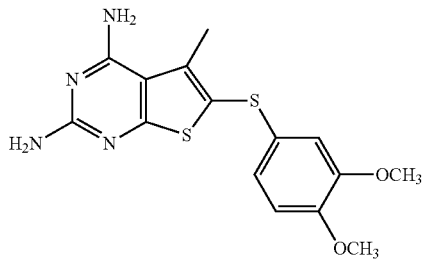 [SMILES: COc1ccc(Sc2sc3nc(N)nc(N)c3c2C)cc1OC]

and optionally comprising a pharmaceutically acceptable salt or hydrate thereof.

In another embodiment of this invention, a pharmaceutical composition is provided comprising a therapeutically effective amount of a compound of the formula:

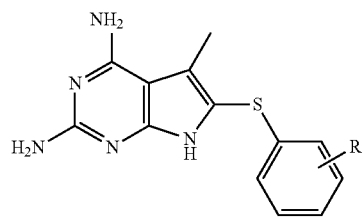

wherein R is 2-OCH$_3$, 3-OCH$_3$, 4-OCH$_3$, or 3,4-diOCH$_3$, and optionally comprising a pharmaceutically acceptable salt or hydrate thereof.

In another embodiment of this invention, a pharmaceutical composition is provided comprising a therapeutically effective amount of a compound of the formula:

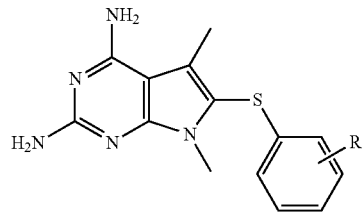

wherein R is 2-OCH$_3$, 3-OCH$_3$, 4-OCH$_3$, or 3,4-diOCH$_3$, and optionally comprising a pharmaceutically acceptable salt or hydrate thereof.

In another embodiment of this invention, a pharmaceutical composition is provided comprising a therapeutically effective amount of a compound of the formula:

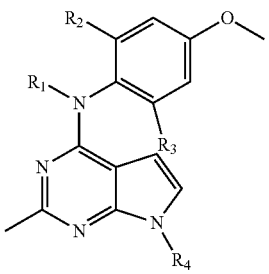

wherein $R_1$ is hydrogen or an alkyl group having from one to ten carbon atoms, $R_2$ is hydrogen or an alkyl group having from one to ten carbon atoms, $R_3$ is hydrogen or an alkyl group having from one to ten carbon atoms, and $R_4$ is hydrogen or an alkyl group having from one to ten carbon atoms, wherein $R_1$, $R_2$, $R_3$, and $R_4$ are independently selected and may be the same or different, and optionally comprising a pharmaceutically acceptable salt or hydrate thereof.

In another embodiment of this invention, a pharmaceutical composition is provided comprising a therapeutically effective amount of a compound of the formula:

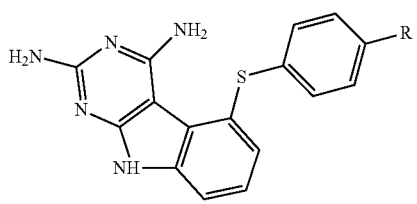

wherein R is hydrogen or an alkyl group having from one to ten carbon atoms, and optionally comprising a pharmaceutically acceptable salt or hydrate thereof.

In another embodiment of this invention, a pharmaceutical composition is provided comprising a therapeutically effective amount of a compound of the formula:

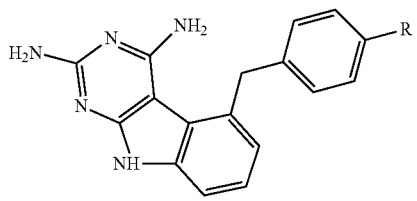

wherein R is hydrogen or an alkyl group having from one to ten carbon atoms, and optionally comprising a pharmaceutically acceptable salt or hydrate thereof.

In another embodiment of this invention, a pharmaceutical composition is provided comprising a therapeutically effective amount of a compound of the formula:

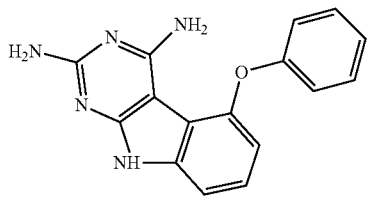 [SMILES: Nc1nc(N)c2c(n1)[nH]c1cccc(Oc3ccccc3)c12]

and optionally comprising a pharmaceutically acceptable salt or hydrate thereof.

In another embodiment of this invention, a pharmaceutical composition is provided comprising a therapeutically effective amount of a compound of the formula:

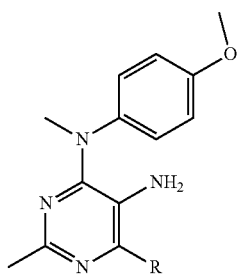

wherein R is hydrogen, an alkyl group having from one to ten carbon atoms, $NH_2$, I, or CN, and optionally comprising a pharmaceutically acceptable salt or hydrate thereof.

In yet another embodiment of this invention, a method of treating a patient having cancer or a disease is provided comprising administering to a patient an effective amount of a compound comprising formula:

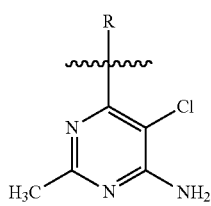

wherein R is selected from one of the following groups consisting of:

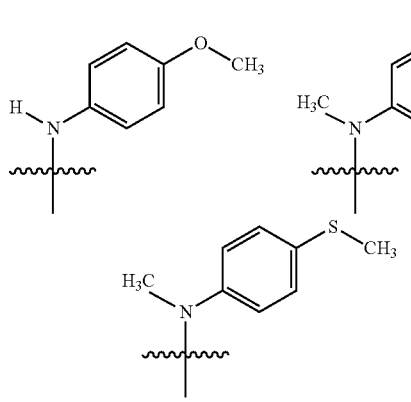

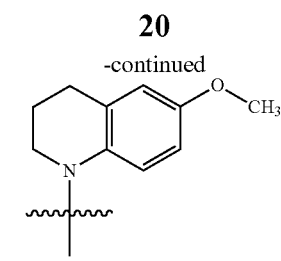

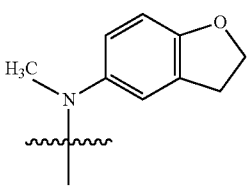

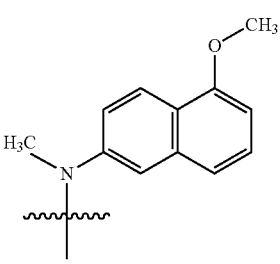

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

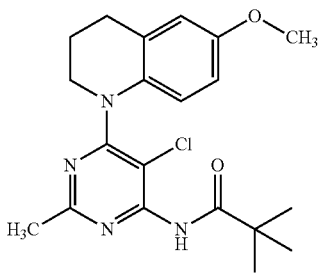 [SMILES: COc1ccc2c(c1)CCCN2c1nc(C)nc(NC(=O)C(C)(C)C)c1Cl]

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

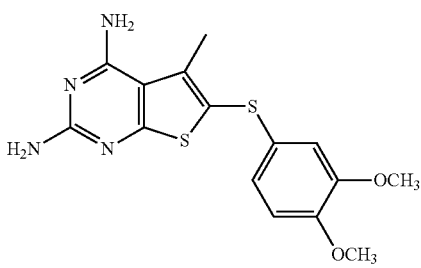 [SMILES: COc1ccc(Sc2sc3nc(N)nc(N)c3c2C)cc1OC]

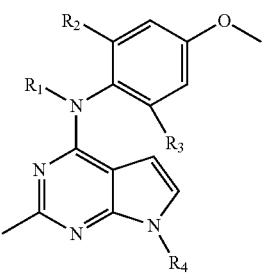

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided having cancer or a disease comprising administering to a patient an effective amount of a compound comprising formula:

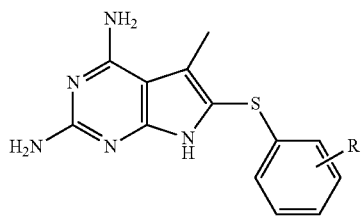

wherein R is 2-OCH$_3$, 3-OCH$_3$, 4-OCH$_3$, or 3,4-diOCH$_3$, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising formula:

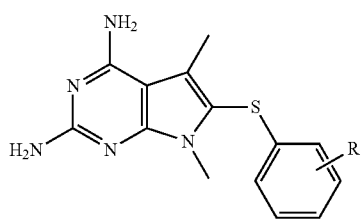

wherein R is 2-OCH$_3$, 3-OCH$_3$, 4-OCH$_3$, or 3,4-diOCH$_3$, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

wherein $R_1$ is hydrogen or an alkyl group having from one to ten carbon atoms, $R_2$ is hydrogen or an alkyl group having from one to ten carbon atoms, $R_3$ is hydrogen or an alkyl group having from one to ten carbon atoms, and $R_4$ is hydrogen or an alkyl group having from one to ten carbon atoms, wherein $R_1$, $R_2$, $R_3$, and $R_4$ are independently selected and may be the same or different, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

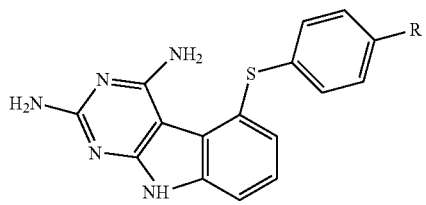

wherein R is hydrogen or an alkyl group having from one to ten carbon atoms, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

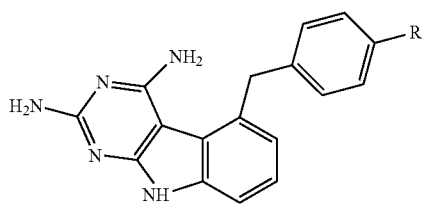

wherein R is hydrogen or an alkyl group having from one to ten carbon atoms, and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

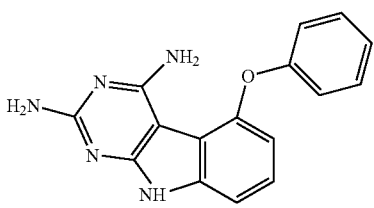 [SMILES: Nc1nc(N)c2c(n1)[nH]c1cccc(Oc3ccccc3)c12]

and optionally comprising a pharmaceutically acceptable salt or hydrate or solvate thereof, and including administering an effective amount of said salt, hydrate, or solvate of said compound to said patient.

In another embodiment of this invention, a method of treating a patient having cancer or a disease is provided comprising administering to a patient an effective amount of a compound comprising the formula:

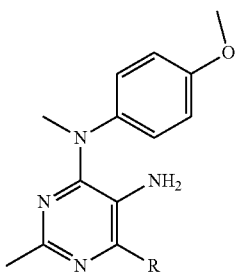

wherein R is hydrogen, an alkyl group having from one to ten carbon atoms, $NH_2$, I, or CN, and optionally comprising a pharmaceutically acceptable salt or hydrate or solvate thereof, and including administering an effective amount of said salt, hydrate, or solvate of said compound to said patient.

A method of treating a patient is provided having a disease comprising administering to a patient an effective amount of one or more of the compounds of this invention. The method includes administering an effective amount of a salt, hydrate, or solvate of at least one of the compound(s) of this invention to the patient.

As used herein, the term "effective amount" is defined as the amount of a compound or composition required to effect a particular result, such as for example, but not limited to, treating a patient for a disease, including cancer.

As used herein, the term "patient" includes all members of the animal kingdom, including but not limited to, *Homo sapiens*, warm and cold blooded animals, and reptiles.

The compounds of this application may be administered to a patient in any suitable pharmaceutical form, with or in any suitable pharmaceutical carrier, and via a suitable route of administration, including for example, but not limited to, the oral route, buccal route, rectal route, parenteral route, intraperitoneal route, intramuscular route, ophthalmic route, dermal route, and inhalation route, to name a few. A pharmaceutically acceptable carrier is any such carrier known to those persons skilled in the art and may include for example but is not limited to saline, dextrose in water, starch, talc, dextrose, or sucrose, and the like.

SECTION A

Design, Synthesis and Biological Evaluation of 6-Amino-5-Chloro-2-Methyl $N^4$-Substituted Pyrimidine Analogs as Anti-Tubulin Agents Structure of an anti-tubulin compound 1 is set forth below:

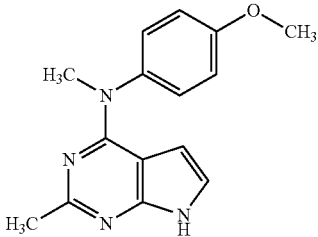

TABLE 1

| Compound No. | $IC_{50}$ MDA-MB-435 (nM) | $EC_{50}$ Microtubule depolymerization (μM) |
| --- | --- | --- |
| 1 | 183 ± 3.4 | 5.8 |

TABLE 2

| | Effect of P-gp on Drug Sensitivity | | |
| --- | --- | --- | --- |
| Compound No. | SK-OV-3 $IC_{50}$ (nM) | SK-OV-3 MDR-1-6/6 $IC_{50}$ (nM) | Rr |
| 1 | 278 ± 19 | 435 ± 33 | 1.6 |
| Paclitaxel | 3.0 ± 0.006 | 2600 ± 270 | 864 |
| CA4P | 4.5 ± 0.2 | 6.6 ± 1.3 | 1.5 |

TABLE 3

| | Effect of β-III Tubulin on Drug Sensitivity | | |
| --- | --- | --- | --- |
| Compound No. | HeLa $IC_{50}$ (nM) | WT β-III $IC_{50}$ (nM) | Rr |
| 1 | 270 ± 21 | 186 ± 17 | 0.7 |
| Paclitaxel | 1.6 ± 0.2 | 7.7 ± 0.2 | 4.7 |
| CA4P | 4.7 ± 0.2 | 5.7 ± 0.4 | 1.2 |

Gangjee et al.[4] had previously reported pyrrolo[2,3-d] pyrimidines as anti-tubulin agents binding to the colchicine binding site. Compound 1 was reported to be a microtubule depolymerizing agent, which inhibited the growth of cancer cells in the nanomolar range (Table 1). This compound further inhibited β-III expressing and P-gp expressing cell lines (Table 2, Table 3).

The present invention provides monocyclic pyrimidine compounds 2-8 (Section A.) with the following structures:

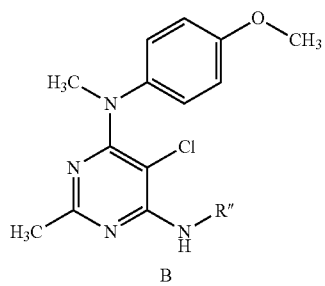

B

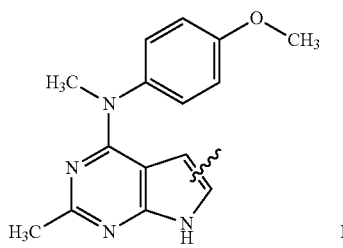

1

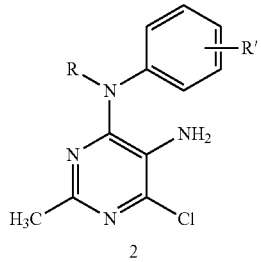

2

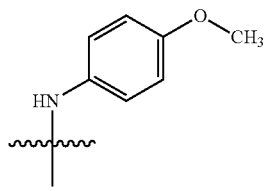

A

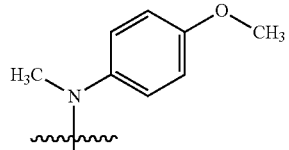

3

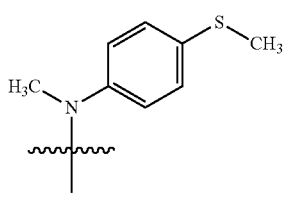

5

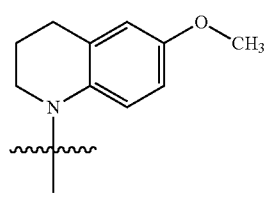

6

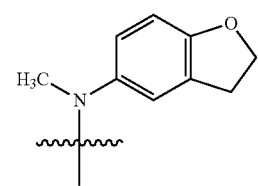

7

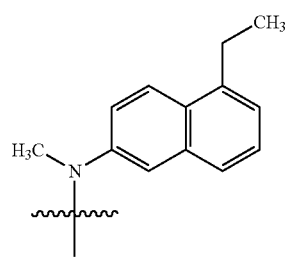

8 wherein R' is —O—CH₃ or —S—CH₃, and R is H or CH₃.

To further explore the requirements of a bicyclic scaffold it was of interest to simplify the structure of compound 1 and determine the minimum structural features that would allow potent cytotoxic and microtubule disrupting activities. To this end the monocyclic pyrimidine analogs derived from the conformationally rigid bicyclic 1 were designed. Based on this strategy Gangjee et al.[5] reported 6-chloro-$N^4$,2-dimethyl-$N^4$-substituted-4,5-diamine of the general structure of compound 2 as a single agent with dual acting antiangiogenic and anti-tubulin activity. The compounds presented here are a continued effort to explore the structure activity relationships (SAR) on the monocyclic pyrimidine core. The effects of interchanging the chlorine and amine substituents at the C5 and C6, thus, altering the electronics of the core scaffold were evaluated. Different anilines were substituted at C4 to determine the optimum substitution.

Syntheses of Section A. Compounds:
The syntheses of compounds 3-7 set forth above are presented in Scheme 1A and Scheme 2A.
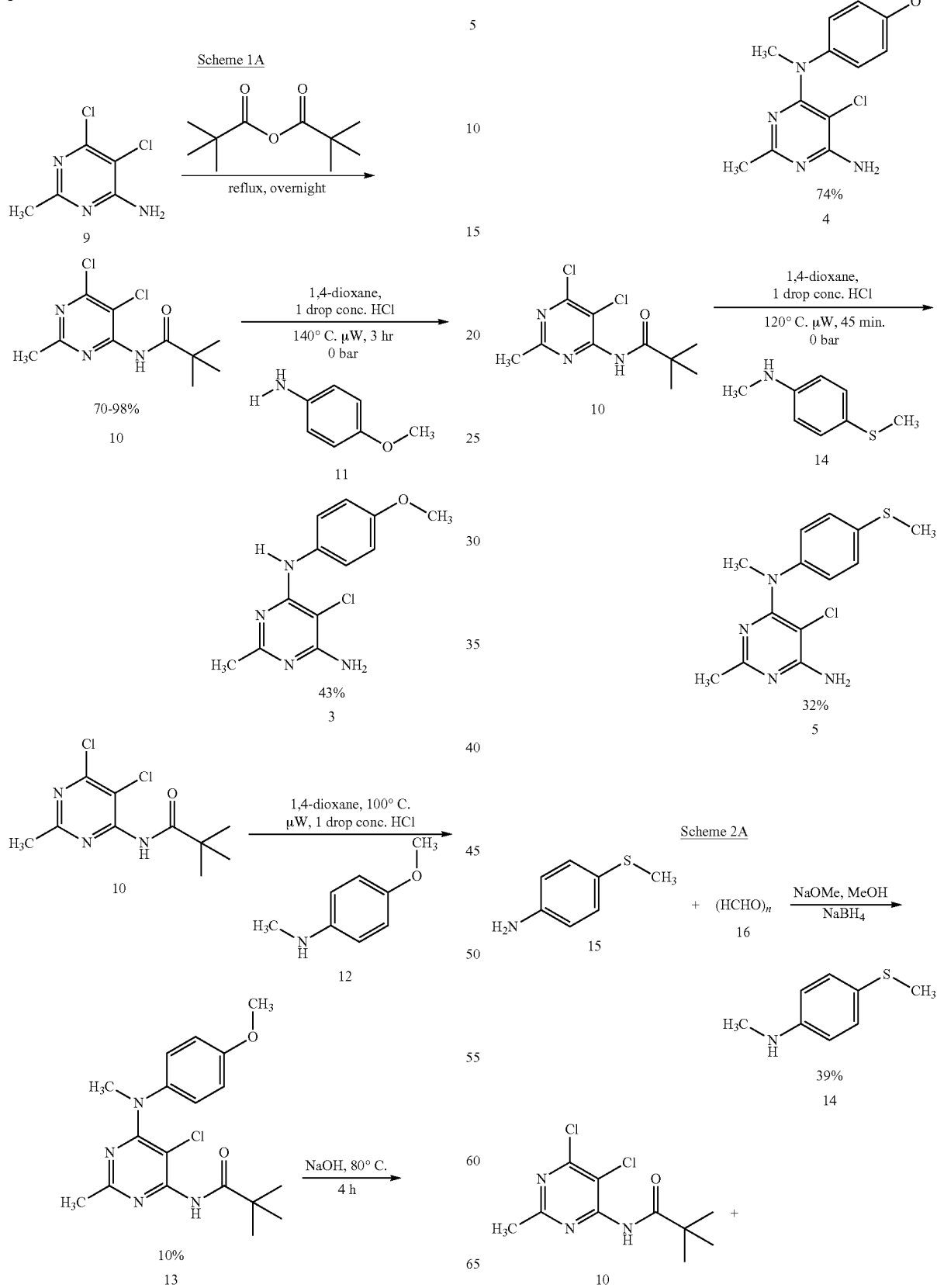

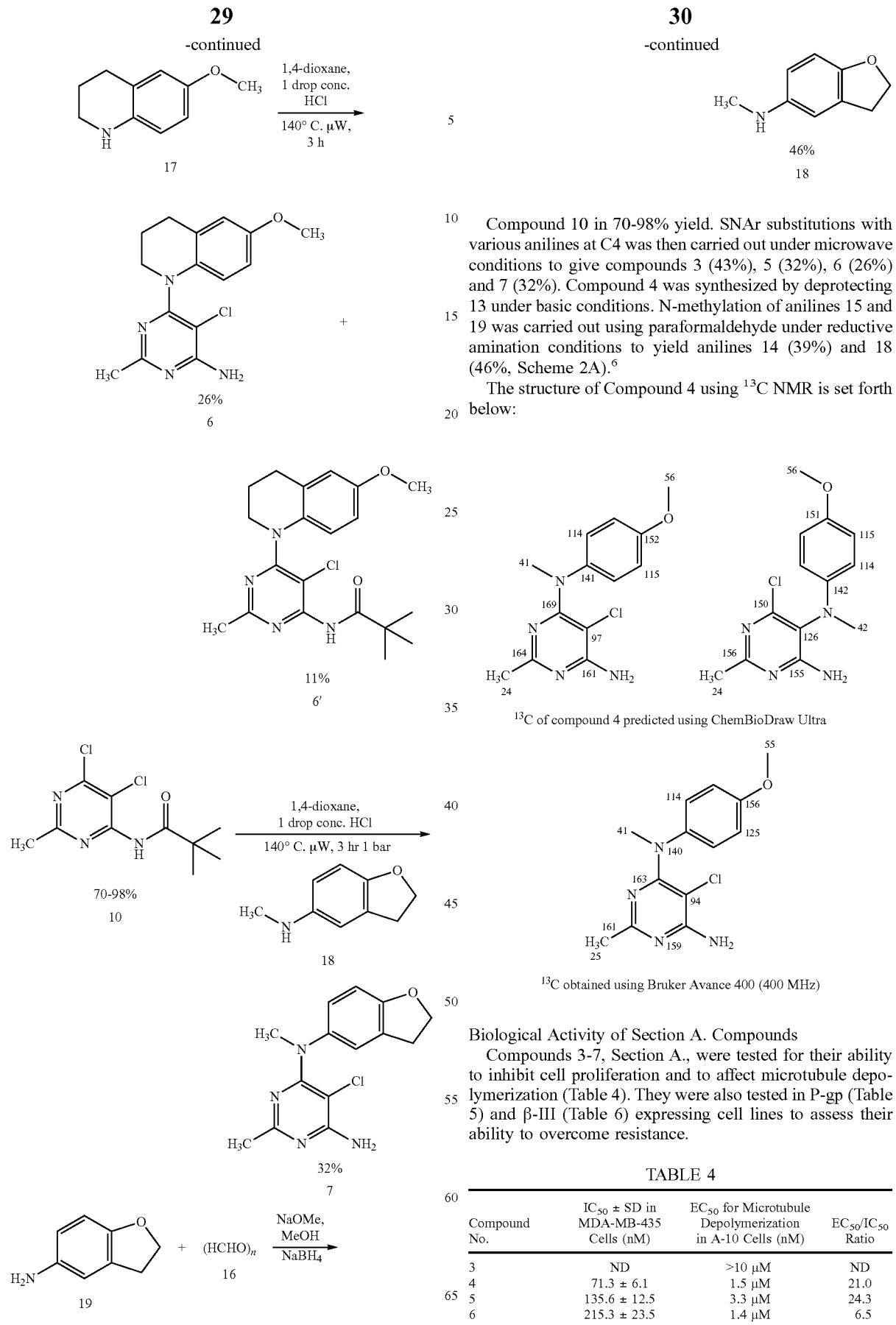

Compound 10 in 70-98% yield. SNAr substitutions with various anilines at C4 was then carried out under microwave conditions to give compounds 3 (43%), 5 (32%), 6 (26%) and 7 (32%). Compound 4 was synthesized by deprotecting 13 under basic conditions. N-methylation of anilines 15 and 19 was carried out using paraformaldehyde under reductive amination conditions to yield anilines 14 (39%) and 18 (46%, Scheme 2A).[6]

The structure of Compound 4 using $^{13}$C NMR is set forth below:

$^{13}$C of compound 4 predicted using ChemBioDraw Ultra $^{13}$C obtained using Bruker Avance 400 (400 MHz)

Biological Activity of Section A. Compounds

Compounds 3-7, Section A., were tested for their ability to inhibit cell proliferation and to affect microtubule depolymerization (Table 4). They were also tested in P-gp (Table 5) and β-III (Table 6) expressing cell lines to assess their ability to overcome resistance.

TABLE 4

| Compound No. | $IC_{50}$ ± SD in MDA-MB-435 Cells (nM) | $EC_{50}$ for Microtubule Depolymerization in A-10 Cells (nM) | $EC_{50}/IC_{50}$ Ratio |
| --- | --- | --- | --- |
| 3 | ND | >10 µM | ND |
| 4 | 71.3 ± 6.1 | 1.5 µM | 21.0 |
| 5 | 135.6 ± 12.5 | 3.3 µM | 24.3 |
| 6 | 215.3 ± 23.5 | 1.4 µM | 6.5 |

TABLE 4-continued

| Compound No. | IC$_{50}$ ± SD in MDA-MB-435 Cells (nM) | EC$_{50}$ for Microtubule Depolymerization in A-10 Cells (nM) | EC$_{50}$/IC$_{50}$ Ratio |
|---|---|---|---|
| 6' | 2,076 ± 464 | 11 μM | 5.3 |
| 7 | in progress | ~10 μM | — |
| Paclitaxel | 4.5 ± 0.52 | — | — |
| CA-4 | 4.4 ± 0.46 | 9.8 | 2.2 |

CA-4 = combretastatin A-4;
ND = not determined

TABLE 5

| | Effect of P-gp on Drug Sensitivity | | |
|---|---|---|---|
| Compound No. | SK-OV-3 IC$_{50}$ (nM) | SK-OV-3 MDR-1-6/6 IC$_{50}$ (nM) | Rr |
| 3 | ND | ND | ND |
| 4 | 112.1 ± 16.4 | 180.2 ± 32.8 | 1.6 |
| 5 | 277.1 ± 13.3 | 414.7 ± 66.2 | 1.5 |
| 6 | 458.8 ± 22.2 | 576.0 ± 42.4 | 1.3 |
| 6' | 3,270 ± 165 | 2,979 ± 52 | 0.9 |
| 7 | in progress | in progress | |
| Paclitaxel | 5.0 ± .6 | 1,200 ± 58 | 240 |
| CA-4 | 5.5 ± 0.5 | 7.2 ± 1.1 | 1.3 |

Rr = relative resistance;
CA-4 = combretastatin A-4;
ND = not determined

TABLE 6

| | Effect of β-III Tubulin on Drug Sensitivity | | |
|---|---|---|---|
| Compound No. | IC$_{50}$ ± SD in HeLa (nM) | IC$_{50}$ ± SD in HeLa WTβ-III (nM) | Rr |
| 3 | ND | ND | ND |
| 4 | 86.3 ± 8.7 | 111.7 ± 9.2 | 1.4 |
| 5 | 158.2 ± 10.6 | 163.3 ± 25.8 | 1.0 |
| 6 | 312.3 ± 41.0 | 278.6 ± 69.0 | 0.9 |
| 6' | *2,490 ± 90.9 | 2,573 ± 418 | * 1.0 |
| 7 | in progress | in progress | |
| Paclitaxel | 2.8 ± .36 | 24.0 ± 3.0 | 8.6 |
| CA-4 | 3.3 ± 0.4 | 3.3 ± 0.3 | 1 |

* n = 2;
Rr = Relative resistance;
CA-4 = Combretastatin A-4;
ND = Not Determined Comparing compounds 3 and 4, section A., it can be said that N$^4$-CH$_3$ substitution is necessary for activity. Compound 5 with a 4'-SCH$_3$ substitution is two fold less potent than compound 4. Pivaloyl group at N6 is not tolerated well as can be seen by comparing activities of compounds 6 and 6'. Amongst all the compounds tested, compound 4 was the most potent compound in this series.

Based on the biological activities, it could be said that these compounds possessed two digits to three digits nanomolar values for inhibition of cell proliferation as exemplified by compounds 4-6, Section A. However, these compounds were not a substrate for resistance by P-gp in that cells lines expressing P-gp were equally sensitive as compared to the parental cell line. The compounds were additionally able to overcome resistance due to the expression of β-III tubulin and hence are effective in multidrug resistant cancer cell lines.

SECTION A. REFERENCES

1. Dumontet, C.; Jordan, M. A. Microtubule-binding agents: a dynamic field of cancer therapeutics. *Nat. Rev. Drug Discov.* 2010, 9, 790-803.
2. Kavallaris, M. Microtubules and resistance to tubulin-binding agents. *Nat. Rev. Cancer* 2010, 10, 194-204.
3. Jordan, M. A.; Wilson, L. Microtubules as a target for anticancer drugs. *Nat. Rev. Cancer* 2004, 4, 253-265.
4. Gangjee, A.; Zhao, Y.; Lin, L.; Raghavan, S.; Roberts, E. G.; Risinger, A. L.; Hamel, E.; Mooberry, S. L. Synthesis and discovery of water-soluble microtubule targeting agents that bind to the colchicine site on tubulin and circumvent Pgp mediated resistance. *J. Med. Chem.* 2010, 53, 8116-8128.
5. Ganjee, A.; Mohan, R.; Bai, R.; Hamel, E.; Inhat, M. Design, synthesis and biological evaluation of substituted monocyclic pyrimidines with dual antiangiogenic and cytotoxic antitubulin activities as antitumor agents. Abstracts of Papers, 246th ACS National Meeting, Indianapolis, Ind., United States, Sep. 8-12, 2013.
6. Teichert, A.; Jantos, K.; Harms, K.; Studer, A. One-pot homolytic aromatic substitutions/HWE olefinations under microwave conditions for the formation of a small oxindole library. *Org. Lett.* 2004, 6, 3477-3480.

SECTION B

6-Substituted Pyrrolo[2,3-D]Pyrimidines as Dihydrofolate Reductase Inhibitors and Potential Anti-Opportunistic Agents

*Pneumocystis jirovecii* (pj), *Toxoplasma gondii*, *Mycobacterium avium* and *M. intracellulare* are some of the most common organisms that cause life-threatening opportunistic infections in AIDS and other immunocompromised patients.[1] Despite the existence of the highly active antiretroviral therapy (HAART), the incidences of HIV cases persist due to nonadherence, toxicity arising from current treatments, emergence of resistant strains, late diagnosis of HIV and a rise in HIV cases in developing countries.[2] *Pneumocystis* pneumonia (PCP) was originally thought to be caused by fungus *Pneumocystis carinii* (pc), but it is now known that the strain that is responsible for infecting humans is *P. jirovecii* (pj). *P. carinii* (pc) is the strain that infects rats.[3]

Dihydrofolate reductase (DHFR) contributes to the de novo mitochondrial thymidylate biosynthesis pathway. DHFR catalyzes the reduction of 7,8-dihydrofolate to 5,6,7,8-tetrahydrofolate using NADPH as reductant. Due to the vital role of DHFR in the folate cycle as well as in thymidylate biosynthesis, the inhibition of DHFR leads to a "thymineless cell death".[4] DHFR enzymes from *P. jirovecii* and *P. carinii* (pc) differ by 38% in amino acid sequence and exhibit different sensitivity to existing drugs.[5] No crystal structure of pjDHFR has been reported to date and known pcDHFR inhibitors act as poor surrogates for pjDHFR inhibition.[6] In addition, difficulties in in-vitro cultures of *P. jirovecii* outside of human lung and the lack of animal models have impeded the drug discovery efforts to obtain a selective pjDHFR inhibitor.[7]

Figure 3:
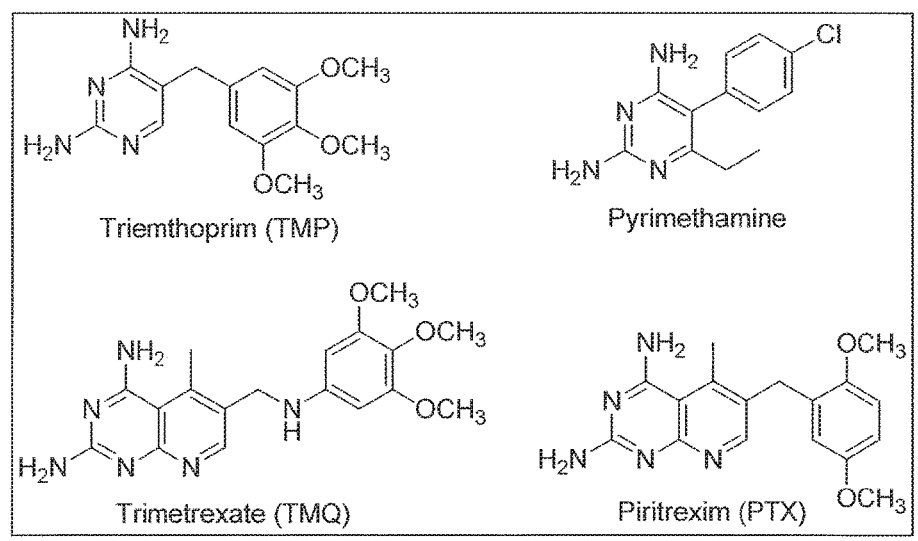
FIG. 3 shows structures of known dihydrofolate reductase inhibitors.

First line therapy of PCP includes lipophilic, non-classical antifolates as trimethoprim (TMP) and pyrimethamine (see FIG. 3—structures of known dihydrofolate reductase inhibitors).[8] Both TMP and pyrimethamine are weak inhibitors of pjDHFR and must be coadministered with sulfonamides to compensate for their weak activities.[1] However, combination therapy is successful only in 50-75% of the AIDS population and is limited due to severe side effects.[9] Trimetrexate (TMQ) and piritrexim (PTX) (FIG. 3) are potent, but non-selective DHFR inhibitors used in the treatment of moderate to severe PCP. However, they cause high rates of myelosuppression and TMQ is coadministered with leucovorin (5-formyltetrahydrofolate) as a rescue agent to prevent host cell toxicity.[10] However, this dual therapy increases treatment cost and host cell rescue with leucovorin is not always successful. Given the limitations of the existing regimen, it is highly desirable to develop single agent DHFR inhibitors that combine the potency of TMQ or PTX with the species selectivity of TMP and would eliminate the need to coadminister sulfonamide or leucovorin. The present invention provides such compounds.

SECTION B. COMPOUNDS

The present invention provides the following compounds: selective pjDHFR inhibitor compound 1, novel DHFR inhibitor compounds 2-5, Section B., and their N7-methyl analogs-compounds 6-9, Section B., as set forth below:

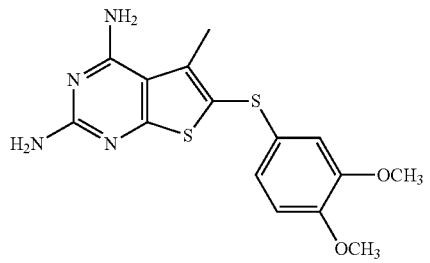

1

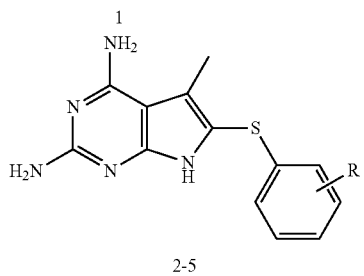

2-5
Series I
2 R = 2-OCH$_3$
3 R = 3-OCH$_3$
4 R = 4-OCH$_3$
5 R = 3,4-diOCH$_3$

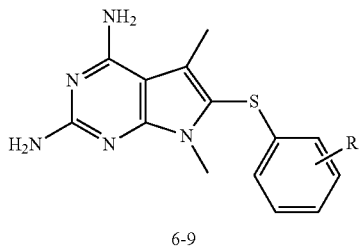

6-9
Series II
6 R = 2-OCH$_3$
7 R = 3-OCH$_3$
8 R = 4-OCH$_3$
9 R = 3,4-diOCH$_3$ In 2013, Gangjee et al.[11] reported a series of 2,4-diamino-5-methyl-6-(arylthio)-thieno[2,3-d]pyrimidines as potent and selective inhibitors of pjDHFR. In this series compound 1 displayed a 3-fold higher selectivity against human derived pjDHFR compared to clinically used TMQ. Compound 1 with a 3,4-dimethoxy substitution in the side-chain aryl moiety shows similarity in the side chain substitution to clinically used TMP, TMQ and PTX. To further explore the structure activity relationship (SAR) of this series of compounds and to optimize the potency and selectivity against pjDHFR and other pathogen DHFR, a series of compounds 2-9 was designed with methoxy group variations in the aryl moiety of compound 1.

Syntheses of Section B. Compounds:

Intermediate compound 12 (Scheme 1B) was prepared by a 2-step procedure reported by Taylor et al.[12] Acetol 10 was condensed with malononitrile in the presence of triethylamine in methanol to afford 2-amino-3-cyano-4-methylfuran (compound 11) which was condensed with guanidine hydrochloride in presence of sodium methoxide to give intermediate (compound 12) in 44% yield. The synthesis of target compounds 2-9, outlined in Scheme 1B, involved oxidative thiolation of the common intermediate 2,4-diamino-5-methyl-pyrrolo[2,3-d]pyrimidine (compound 12) with appropriately substituted thiols. Compounds 2-5 were synthesized from compound 12 with slight modification of the oxidative thiolation previously reported by Gangjee et al.[13] This procedure involved reacting compound 12 with appropriately substituted thiols and iodine in a 2:1 mixture of ethanol and water at reflux to give compounds 2-5. Compounds 6-9 were synthesized by methylation of the pyrrole nitrogen using sodium hydride and iodomethane.

Scheme 1B: Synthetic route to novel DHFR inhibitor compounds 2-5 and their N7-methyl analog compounds 6-9:

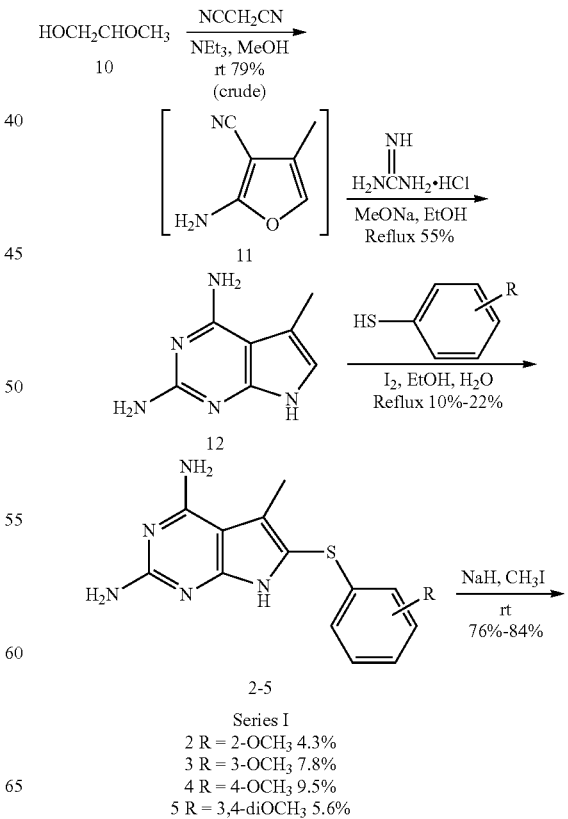

-continued

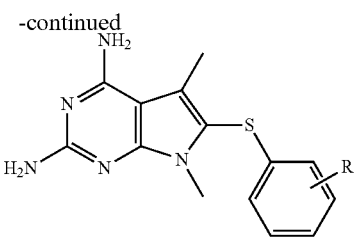

6-9
Series II
6 R = 2-OCH$_3$ 3.3%
7 R = 3-OCH$_3$ 6.24%
8 R = 4-OCH$_3$ 7.98%
9 R = 3,4-diOCH$_3$ 4.4%

Biological Activity of Section B. Compounds:

TABLE 7

Inhibitory concentrations (IC$_{50}$, in µM) against recombinant pjDHFR, human DHFR (hDHFR) and selectivity ratios [a]

| Compound No. | pjDHFR IC$_{50}$ (µM) | hDHFR IC$_{50}$ (µM) | Selectivity hDHFR/pjDHFR |
|---|---|---|---|
| 1 | 0.260 | 0.910 | 3.5 |
| 2 | 0.177 | 0.624 | 3.53 |
| 3 | 0.213 | 0.97 | 4.55 |
| 4 | 0.252 | 1.41 | 5.66 |
| 5 | 3.900 | 6.9 | 1.80 |
| 6 | 0.210 | 1.4 | 6.7 |
| 7 | 0.160 | 1.9 | 11.9 |
| 8 | — | — | — |
| 9 | 0.234 | 1.1 | 4.70 |
| TMP[b] | 0.120 | 32.2 | 268 |
| TMQ[b] | 0.0021 | 0.0026 | 1.2 |

[a] These assays were carried out at 37° C. under 9 µM dihydrofolic acid concentration
[b] These assays were carried out at 37° C. under 18 µM dihydrofolic acid concentration Compounds 2-9 of Section B. were evaluated as inhibitors of pjDHFR and hDHFR and the results are reported in Table 7. Selectivity ratios, expressed as IC$_{50}$ against hDHFR/IC$_{50}$ against pjDHFR (h/pj) are also listed in Table 7. The inhibitory activities of TMP and TMQ are listed for comparison. While the tested compounds displayed reduced potency against pjDHFR compared to TMQ, they showed 2 to 5 fold greater selectivity. On comparison of the compounds from the two series of Section B. compounds, as observed in compound pairs 2 and 6, 3 and 7 and 5 and 9, methylation of the pyrrole nitrogen improved the selectivity ratios by 2 to 3 fold. Compound 7, the most selective compound in the series of compounds of this Section B, was about 10-fold more selective for pjDHFR over hDHFR than TMQ. None of the compounds synthesized exhibited potency greater than TMQ, but had greater selectivity compared to TMQ.

SECTION B. REFERENCES

1. Kaplan, J. E.; Benson, C.; Holmes, K. H.; Brooks, J. T.; Pau, A.; Masur, H. Centers for Disease Control and Prevention (CDC); National Institutes of Health; HIV Medicine Association of the Infectious Diseases Society of America: Guidelines for prevention and treatment of opportunistic infections in HIV-infected adults and adolescents: recommendations from CDC, the National Institutes of Health, and the HIV Medicine Association of the Infectious Diseases Society of America. *MMWR Recomm. Rep.* 2009, 58, 1-207.

2. a) Catherinot, E.; Lanternier, F.; Bougnoux, M. E.; Lecuit, M.; Couderc, L. J.; Lortholary, O. Pneumocystis jirovecii pneumonia. *Infect. Dis. Clin. N. Am.* 2010, 24, 107-138. b) Ong, E. L. C. Common AIDS-Associated Opportunistic Infections. *Clinical Medicine* 2008, 8, 539-543.

3. Gangjee, A.; Kurup, S.; Namjoshi, O. Dihydrofolate reductase as a target for chemotherapy in parasites. *Curr. Pharm. Des.* 2007, 13, 609-639.

4. MacKenzie, R. E. Biogenesis and interconversion of substituted tetrahydrofolates. in *Folates and Pterins Chemistry and Biochemistry*; Blakley, R. L., Benkovic, S. J., Eds.; Wiley: New York, 1984; Vol. I, 255-306.

5. Ma, L.; Kovacs, J. A. Expression and characterization of recombinant human-derived Pneumocystis carinii dihydrofolate reductase. *Antimicrob. Agents Chemother.* 2000, 44, 3092-3096.

6. Cody, V.; Chisum, K.; Pope, C.; Queener, S. F. Purification and characterization of human-derived Pneumocystis jirovecii dihydrofolate reductase expressed in Sf21 insect cells and in Escherichia coli. *Protein Expr. Purif.* 2005, 40, 417-423.

7. Thomas, C. F.; Limper, A. H. Current insights into the biology and pathogenesis of Pneumocystis Pneumonia. *Nat. Rev. Microbio.* 2007, 5, 298-308.

8. Klepser, M. E.; Klepser, T. B. Drug treatment of HIV-related opportunistic infections. *Drugs* 1997, 53, 40-73.

9. Roudier, C.; Caumes, E.; Rogeaux, O.; Bricaire, F.; Gentilini M. Adverse cutaneous reactions to trimethoprim-sulfamethoxazole in patients with the acquired immunodeficiency syndrome and Pneumocystis carinii pneumonia. *Arch. Dermatol.* 1994, 130, 1383-1386.

10. Allegra, C. J.; Kovacs, J. A.; Drake, J. C.; Swan, J. C.; Chabner, B. A.; Masur, H. Activity of antifolates against Pneumocystis carinii dihydrofolate reductase and identification of a potent new agent. *J. Exp. Med.* 1987, 165, 926-931.

11. Gangjee, A.; Choudhary, S.; Zhou, X.; Queener, S. F.; Cody, V. Design, synthesis and biological evaluation of substituted thieno[2,3-d]pyrimidines as dihydrofolate reductase inhibitors and potential anti-opportunistic agents. Abstracts of Papers, 246th ACS National Meeting, Indianapolis, Ind., United States, Sep. 8-12, 2013

12. Taylor, E. C.; Patel, H. H.; Jun, J. G. A one-step ring transformation/ring annulation approach to pyrrolo[2,3-d]pyrimidines. A new synthesis of the potent dihydrofolate reductase inhibitor TNP-351. *J. Org. Chem.* 1995, 60, 6684-6687.

13. Gangjee, A.; Devraj, R. D.; McGuire, J. J.; Kisliuk, R. L. 5-Arylthiosubstituted 2-amino-4-oxo-6-methyl-pyrrolo[2,3-d]pyrimidine antifolates as thymidylate synthase inhibitors and antitumor agents. *J. Med. Chem.* 1995, 38, 4495-4501.

SECTION C

Conformationally Restricted Pyrrolo[2,3-d]Pyrimidines as Potential Antimitotic and Antitumor Agents Disruption of cellular microtubules is a validated target for cancer.[1] Three major classes of microtubule active agents (see FIG. 1) have been identified according to their binding site on tubulin.[2] Vinca alkaloids such as vincristine, vinblastine consist of the first group which are microtubule destabilizers. These are β-tubulin binding agents used in leukemias, lymphomas and other cancers. The second group consist of the taxoids such as paclitaxel and docetaxel which are designated as microtubule stabilizing agents. These agents bind at the interior surface of β-subunit of microtubules. They are useful against breast, lung, ovarian and prostate carcinomas. The third group is typified by colchicine which comprise of a diverse collection of molecules which bind at the β-tubulin at its interface with α-tubulin. This class of antimitotic agents is also known as microtubule destabilizers.[3] Combretastatin A-4 (CA4) and its phosphorylated analog combretastatin A-4 phosphate (CA4-P) which binds to the colchicine site on tubulin is currently in clinical trials. There are no approved colchicine site binding agents. This demonstrates the importance of developing colchicine site agents as antitumor agents.[4,5]

Mutations in the p53 gene occurs in half of all tumors and tubulin binding agents are highly effective in treating p53 mutant cells.[6] Multidrug resistance (MDR) is a major limitation in cancer chemotherapy, and MDR tumors are resistant to many tubulin-binding agents.[7] Overexpression of P-glycoprotein (Pgp) has also been reported in a number of tumor types.[8] Attempts to reverse drug resistance by combining antimitotic agents with inhibitors of drug efflux proteins produced disappointing results.[3] Expression of βIII-tubulin is another mechanism of resistance to tubulin binding agents in multiple tumor types including non-small cell lung,[9] breast[10] and ovarian cancer.[11] Stengel et al.[12] showed that colchicine site binding agents are the most effective agents against βIII-tubulin expressing cells which further demonstrates the importance of developing this class of agents.

SECTION C. COMPOUNDS

The present invention provides the following compounds 2-9:

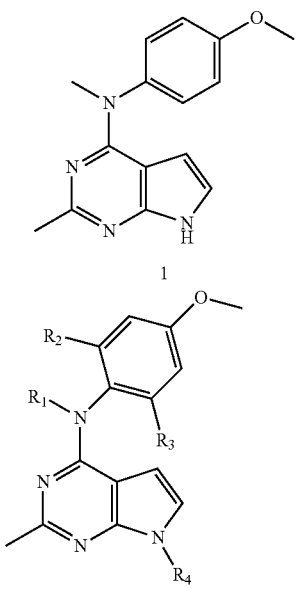

2. $R_1$ = H, $R_2$ = H, $R_3$ = H, $R_4$ = H
3. $R_1$ = $CH_3$, $R_2$ = H, $R_3$ = H, $R_4$ = $CH_3$
4. $R_1$ = H, $R_2$ = $CH_3$, $R_3$ = H, $R_4$ = H
5. $R_1$ = $CH_3$, $R_2$ = $CH_3$, $R_3$ = H, $R_4$ = H
6. $R_1$ = H, $R_2$ = $CH_3$, $R_3$ = $CH_3$, $R_4$ = H
7. $R_1$ = $CH_3$, $R_2$ = $CH_3$, $R_3$ = $CH_3$, $R_4$ = H
8. $R_1$ = H, $R_2$ = $CH_3$, $R_3$ = $CH_3$, $R_4$ = $CH_3$
9. $R_1$ = $CH_3$, $R_2$ = $CH_3$, $R_3$ = $CH_3$, $R_4$ = $CH_3$

In 2010, Gangjee et al.[13] reported pyrrolo[2,3-d]pyrimidine (compound 1, Section C.) as an inhibitor of the proliferation of human cancer cells (MDA-MB-435). Compound 1, Section C., inhibits the growth of cancer cells with $GI_{50}$ values in the nanomolar range and also circumvents Pgp and βIII-tubulin mediated resistance mechanisms that limit the activity of several microtubule targeting agents.[13] However, compound 2, Section C., the N-desmethyl analog of compound 1, is inactive in the cancer cells evaluated thus far. The activity of compound 1 was suggested in part, to involve the 4N-methyl group of compound 1 that aids in maintaining the relative conformations of the pyrrolo[2,3-d]pyrimidine scaffold and the phenyl ring.[13] To further extend this finding, a series of conformationally restricted analogs, compounds 3-9 of this Section C. were designed based on a systematic approach to restrict the conformation of the phenyl ring relative to the bicyclic pyrrolo[2,3-d]pyrimidine scaffold. A conformational search carried out using Sybyl 2.1.1 for energy minimized structures of compounds 1,5, and 7, Section C., indicated that, compared to compound 1, the number of low energy conformations were lowered in compound 5. In compound 7 the number of low energy conformations were further lowered. Compound 3, Section C. was designed based on a docking study (not shown) using LeadIT 2.1[14] which indicated that a potential hydrophobic interaction with Val181 in the colchicine site of tubulin could be achieved by introducing a methyl group at the N7 position, which was expected to improve tubulin inhibitory activity. The docking studied showed a stereoview of a superimposition of the docked poses of compound 3 and DAMA colchicine in the colchicine site of tubulin at the interface of the α-subunit (magenta) and β-subunit (blue) of tubulin.

Chemistry of Section C. Compounds

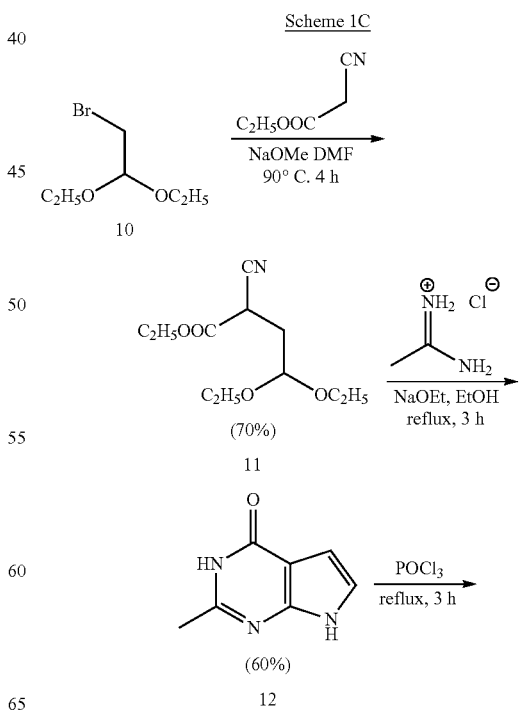

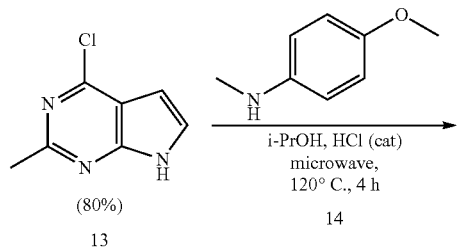
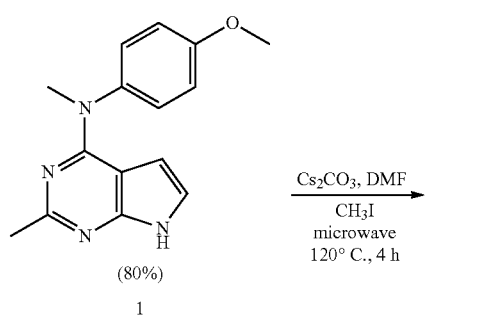
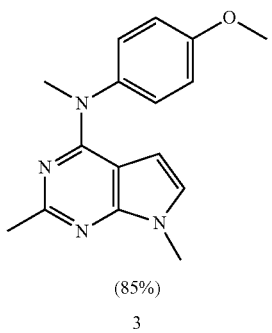
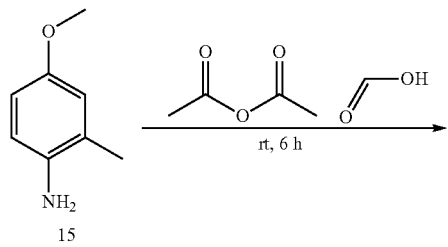
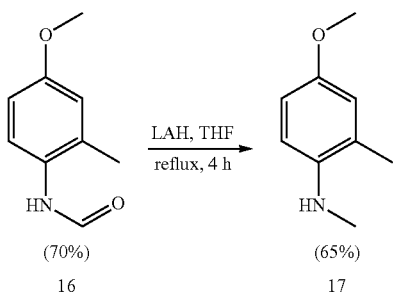
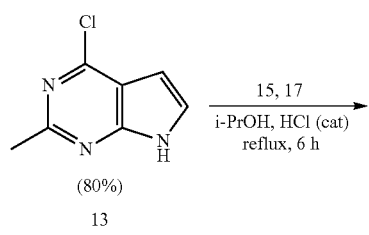

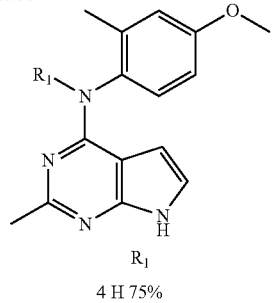

4 H 75%
5 CH3 70%

The synthesis of target compound 3 (Scheme 1C), started with the synthesis of a reported method for compound 1.[13] 2-Bromo-1,1-diethoxyethane (compound 10) was reacted with ethyl-2-cyanoacetate to obtain compound 11 which was cyclized to compound 12 using acetamidine hydrochloride under basic conditions. Chlorination of compound 12 using POCl$_3$ provided compound 13 in 80% yield. Displacement of the chloride of compound 13 with 4-methoxy-N-methyl aniline (compound 14) and catalytic amounts of HCl in isopropanol, provided compound 1. Methylation of compound 1 with MeI under basic conditions afforded compound 3 in 85% yield. The synthesis of target compound 5 (Scheme 1C), involved N-formylation of 4-methoxy-2-methylanline (compound 15) to afford compound 16 in 70% yield. LAH reduction of compound 16 provided substituted aniline compound 17. Displacement of the chloride of compound 13 with anilines (compounds 15 and 17) and catalytic amounts of HCl in isopropanol provided compounds 4 and 5 (75% and 70% respectively).

Scheme 2C

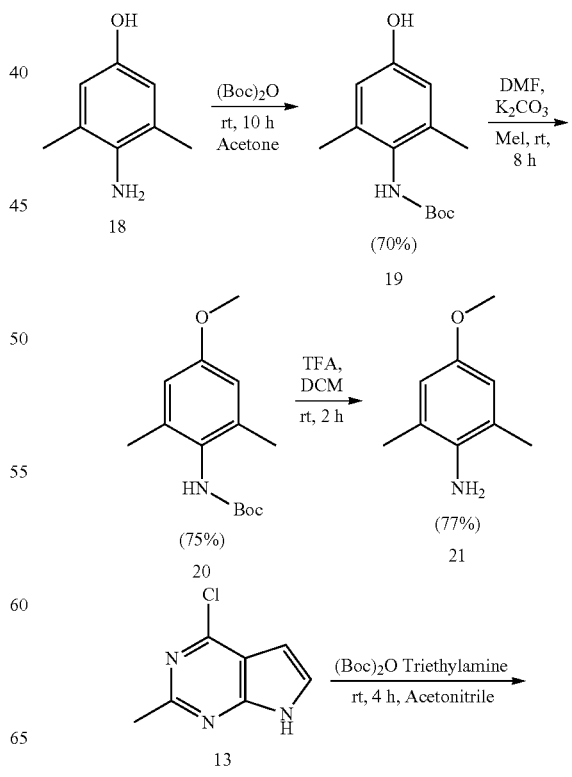

-continued

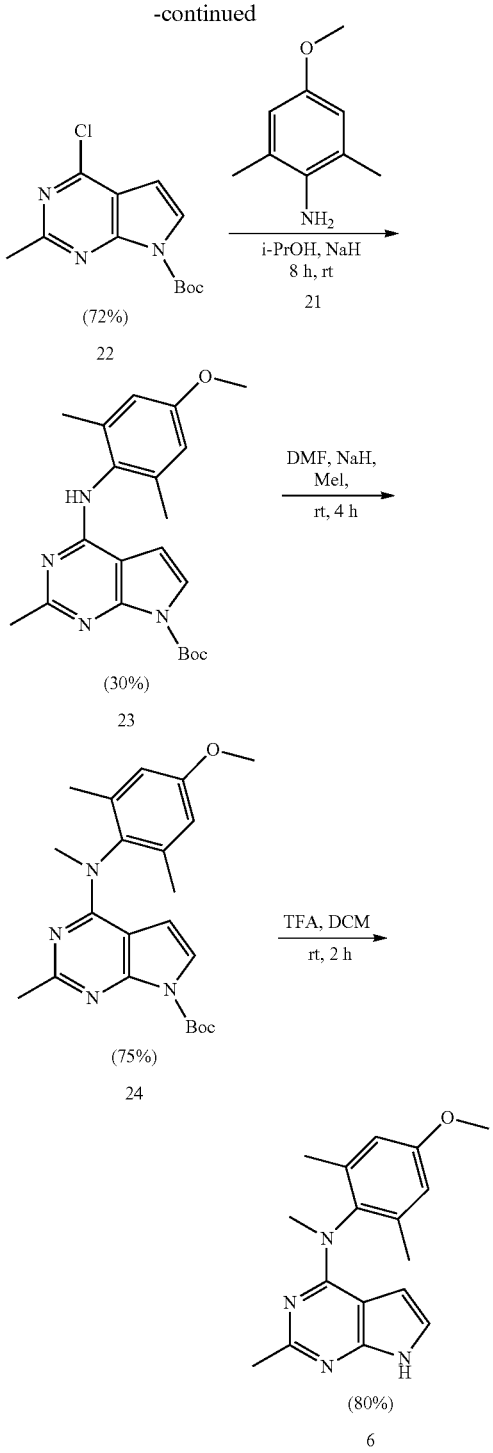

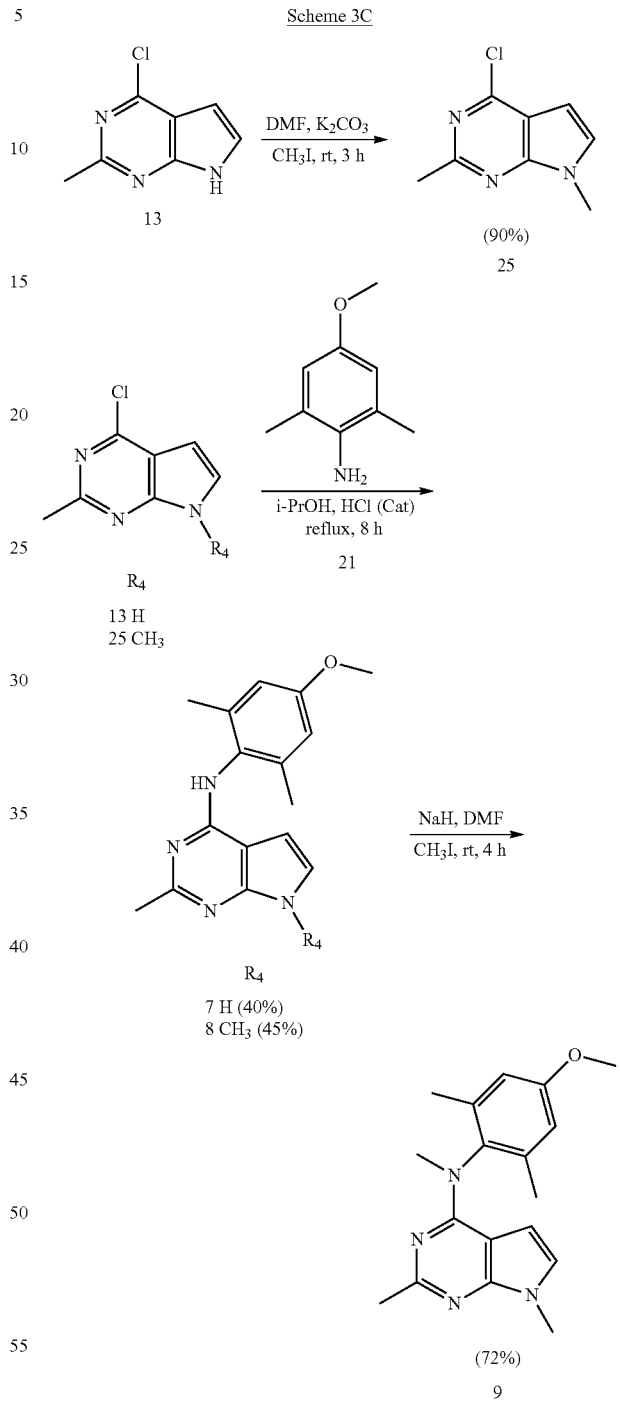

of compound 23 with MeI followed by deprotection provided desired compound 6, Section C.

The synthesis of compound 6, Section C., started from 4-amino-3,5-dimethylphenol (compound 18, Scheme 2C). Boc anhydride was used to protect the amino group of compound 18 to obtain compound 19 in 70% yield. Methyl iodide was used to alkylate the free hydroxyl group of compound 19, to afford compound 20 in 75% yield. Deprotection using trifluoro acetic acid in DCM gave the desired aniline compound 21. The pyrrole nitrogen of compound 13 was Boc protected to obtain compound 22. Displacement of the chloride of compound 22 with compound 21 under basic condition furnished compound 23 in 30% yield. Methylation The synthesis of compound 7-9, section C., of this invention are shown in Scheme 3C. The pyrrole nitrogen of compound 13 was methylated with MeI to obtain compound 25. Displacement of the chloride of compounds 13 and 25 with compound 21 under acidic conditions provided the desired compounds 7 and 8 in 40-45% yield respectively. Further methylation of compound 8 by iodomethane under basic conditions gave compound 9 in 72% yield.

Biological Activity of Section C. Compounds:

TABLE 8

IC$_{50}$ Values For Inhibition Of Proliferation Of Mda-Mb-435 Cells And Effect On Microtubule Polymerization

| COMPOUND | IC$_{50}$ ± SD (MDA-MB-435) TUMOR CELLS | EC$_{50}$ IN A-10 CELLS (TUBULIN POLYMERIZATION INHIBITORY ACTIVITY) |
|---|---|---|
| 1 | 183 ± 3.4 NM | 5.8 MM |
| 2 | >10 MM | >40 MM |
| 3 | 63.2 ± 4.7 NM | 1.02 MM |
| 4 | ND | >10 MM |
| 5 | ND | >10 MM |
| 6 | ND | >10 MM |

ND = NOT DETERMINED

Compounds 3-6, Section C., were tested for antiproliferative effects against the mda-mb-435 tumor cell line using sulforhodamine b assay (srb assay). Microtubule disrupting effects of compounds 3-6 were evaluated in a cell-based phenotypic screen. Compounds 4-6 did not show depolymerization of microtubules upto 10 μm indicating that compounds 4-6 were inactive. Compound 3, Section C., however caused depolymerization of microtubules and was 5-fold more potent than compound 1, section C., and inhibited mda-mb-435 tumor cells with a 2-fold better IC$_{50}$ than compound 1. Based on the potent activity of compound 3, Section C., compounds 8 and 9 with n7-CH$_3$ groups were synthesized along with a n7-H compound 7.

A proton NMR study was carried out, to explore the conformations of 2, 3, 5 and 7 which can be considered a representative example of the series of compounds (compounds 1-9). $^1$H NMR spectra for compounds 2, 3, 5, and 6 (not shown, having a scale from δ10.0-δ4.0 ppm) in DMSO-d6 was obtained. The $^1$H NMR spectra for compound 2 shows that the sigma bonds (c$_1$·-n and n-c$_4$) connecting the phenyl ring and pyrrolo[2,3-d]pyrimidine ring are both freely rotatable, while these bonds are restricted in compounds 3, 5, and 7, where an additional methyl group was introduced on the n-4 position. According to $^1$h nmr spectrum (not shown), the 5-h proton in compounds 3, 5, and 7 (δ 4.53, δ4.39 and δ4.37 ppm respectively) are more shielded than compound 2 (δ6.55 ppm), which suggests a nearby shielding diamagnetic anisotropic cone. Due to the bulk of the 4-n-methyl group, the conformations of compounds 3, 5, and 7 are also restricted such that the phenyl ring has to position itself on top of the 5-h proton, which leads to the observed shielding effect in compounds 3, 5, and 7.

Compound 3, Section C., in which the pyrrole is n-methylated, shows better microtubule depolymerization potency than compound 1, Section C. The role of the n7-methyl group to increase activity may be an additional hydrophobic interaction with the active site val181 (supported by the docking study) that is lacking in compounds 4-6 and is responsible for the potent activity of compound 3, Section C. In addition, the 4n-methyl moiety in compound 3 also plays a role in its potent activity. Inactivity of compound 5 suggests that the conformationally restricted form of compound 5 may not be the bioactive conformation.

SECTION C. REFERENCES

1. Jordan, M. A.; Wilson, L. Microtubules as a Target for Anticancer Drugs. *Nat. Rev. Cancer* 2004, 4, 253-265.
2. Jordan, M. A.; Kamath, K. How do Microtubule-Targeted Drugs Work? An Overview. *Curr. Cancer Drug Targets* 2007, 7, 730-742.
3. Dumontet, C; Jordan, M. A. Microtubule-binding agents: A Dynamic Field of Cancer Therapeutics *Nat. Rev. Drug Discov.* 2010, 9, 790-803.
4. Kanthou, C.; Tozer, M. T. Microtubule Depolymerizing Vascular Disrupting Agents: Novel Therapeutic Agents for Oncology and Other Pathologies. *Int. J. Exp. Pathol.* 2009, 90, 284-294.
5. Carlson, R. O. New Tubulin Targeting Agents Currently in Clinical Development *Expert Opin. Investig. Drugs* 2008, 17, 707-722.
6. Kavallaris, M. Microtubules and resistance to tubulin-binding agents. *Nat. Rev. Cancer,* 2010, 3, 194-204.
7. Ling, V. Multidrug Resistance: Molecular Mechanisms and Clinical Relevance. *Cancer Chemother.* 1997, 40, S3-8.
8. Chiou, J. F.; Liang, J. A.; Hsu, W. H.; Wang, J. J.; Ho, S. T.; Kao, A. Comparing the Relationship of Taxol-based Chemotherapy Response with P-glycoprotein and Lung Resistance-related Protein Expression in Non-Small Cell Lung Cancer. *Lung* 2003, 181, 267-273.
9. Seve, P.; Isaac, S.; Tredan, O.; Souquet, P.-J.; Pacheco, Y.; Perol, M.; Lafanechere, L.; Penet, A.; Peiller, E.-L.; Dumontet, C. Expression of Class III β-Tubulin Is Predictive of Patient Outcome in Patients with Non-Small Cell Lung Cancer Receiving Vinorelbine-Based Chemotherapy. *Clin. Cancer Res.* 2005, 11, 5481-5486.
10. Tommasi, S.; Mangia, A.; Lacalamita, R.; Bellizzi, A.; Fedele, V.; Chiriatti, A.; Thomssen, C.; Kendzierski, N.; Latorre, A.; Lorusso, V.; Schittulli, F.; Zito, F.; Kavallaris, M.; Paradiso, A. Cytoskeleton and Paclitaxel Sensitivity In Breast Cancer: The Role Of Beta-Tubulins. *Int. J. Cancer* 2007, 120, 2078-2085.
11. Ferrandina, G.; Zannoni, G. F.; Martinelli, E.; Paglia, A.; Gallotta, V.; Mozzetti, S.; Scambia, G.; Ferlini, C. Class III β-Tubulin Overexpression Is A Marker Of Poor Clinical Outcome In Advanced Ovarian Cancer Patients. *Clin. Cancer Res.* 2006, 12, 2774-2779.
12. Stengel, C; Newman, S. P.; Lesse, M. P.; Potter, B. V. L.; Reed, M. J.; Purohit, A. Class III Beta-Tubulin Expression and in vitro Resistance To Microtubule Targeting Agents. *Br. J. Cancer* 2010, 102, 316-324.
13. Gangjee, A.; Zhao, Y; Lin, L.; Raghavan, S.; Roberts, E. G.; Risinger, A. L.; Hamel, E.; Mooberry S. L. Synthesis and Discovery of Water-Soluble Microtubule Targeting Agents that Bind to the Colchicine Site on Tubulin and Circumvent Pgp Mediated Resistance. *J. Med. Chem.* 2010, 53, 8116-8128.
14. LeadIT, version 2.1; BioSolveIT GmbH: Sankt Augustin, Germany.
15. Ravelli, R. B.; Gigant, B.; Curmi, P. A.; Jourdain, I.; Lachkar, S.; Sobel, A.; Knossow, M. *Nature,* 2004, 428, 198-202.

SECTION D

Figure 4:
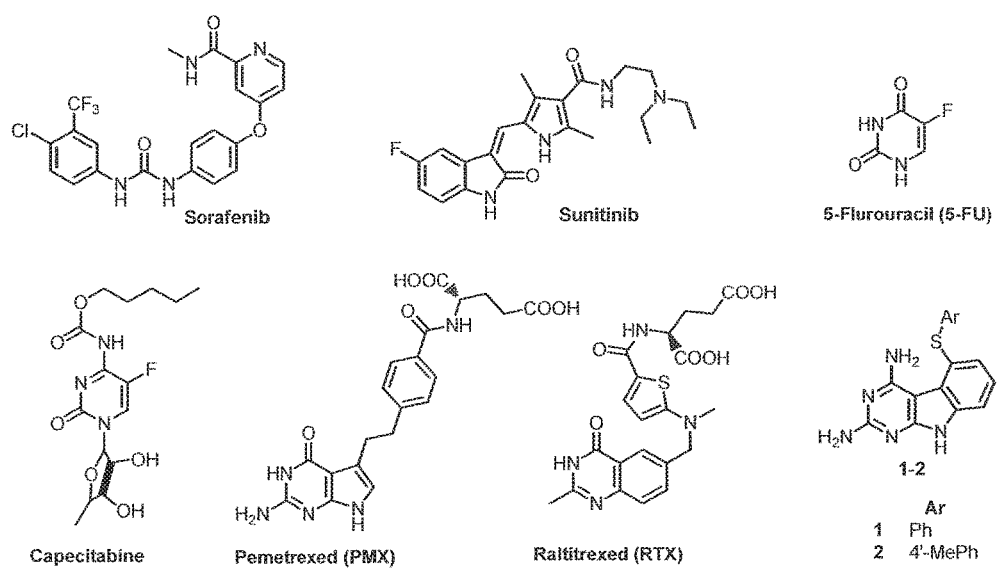
FIG. 4 shows structures of inhibitors of thymidylate synthase.

5-Substituted Pyrimido[4,5-b]Indoles with Single Agent Combination Chemotherapeutic Potential Thymidylate synthase (TS) converts dUMP (deoxyuridine monophosphate) to dTMP (deoxythymidine monophosphate) by transferring a methyl group via the cofactor 5,10-methylenetetrahydrofolate. This is an important step for DNA synthesis and cell growth, thus TS is a viable target for several clinically used cancer chemotherapeutic agents.[1,2] The fluoropyrimidine, 5-fluorouracil (5-FU) and its derivatives, in particular, capecitabine (FIG. 4), have found extensive utility in ovarian, breast, colon, and several other cancers alone and in combinations and are a mainstay in cancer chemotherapy.[3] Folate inhibitors of TS, pemetrexed (PMX)[4] and in Europe raltitrexed (RTX)[5], are used alone or in combination in the clinic against a variety of cancers (see FIG. 4 structures).

Angiogenesis is the process of formation of new blood vessels from existing vasculature—is essential for tumor growth and metastasis.[6] Receptor tyrosine kinases (RTKs) play a crucial role in angiogenesis. RTKs are enzymes that catalyze the transfer of the γ-phosphate of ATP to tyrosine residues of protein substrates. Vascular endothelial growth factor receptor (VEGFR), epidermal growth factor receptor (EGFR) and platelet derived growth factor receptor (PDGFR) are common RTKs that are overexpressed in cancer cells.[7] Agents that block angiogenesis by inhibition of RTKs have established a new paradigm in cancer chemotherapy. Single RTK inhibitors are prone to resistance by numerous mechanisms including point mutations in the ATP binding site and upregulation of additional RTKs.[8] Consequently multi-RTK inhibition in cancer chemotherapy has emerged as a promising approach and its validity has been highlighted by the approval of several multi-RTK inhibitors including sorafenib [inhibits VEGFR-2, PDGFR-β, Flt-3 (FMS-like tyrosine kinase-3), Raf kinase and c-kit][9] and sunitinib [inhibits VEGFR-1, -2, and -3, PDGFR-β, -α, stem cell factor (kit), Flt-3 and CSF-1R (colony-stimulating factor-1 receptor)] (FIG. 1).[10]

Combination cancer chemotherapy is not a novel concept. Recent studies suggest that the combination of separate cytostatic, antiangiogenic agents with separate cytotoxic agents is more effective in cancer chemotherapy than either agent alone.[11] We envisioned the design of single agents that would function by both a cytostatic (antiangiogenic) mechanism and a cytotoxic (antifolate) mechanism. Such single agents would circumvent the pharmacokinetic problems of two or more agents and reduce drug-drug interactions. In addition, the same agents could be used at lower doses to alleviate toxicity, be devoid of overlapping toxicities, and delay or prevent tumor cell resistance. Most significantly, providing the cytotoxic agent, by structural design, in the same molecule allows the cytotoxicity to be manifested as soon as the antiangiogenic effects are operable.

A separately dosed cytotoxic agent may miss the timing window and hence thwart the intent of the combination. Such multi-targeted agents could wield their cytotoxic action as soon as or even during transient tumor vasculature normalization[9,10] due to the antiangiogenic effects. Thus such agents, perhaps, do not need to be as potent as conventional, separately dosed cytotoxic agents. Other advantages of such single agents are in the decreased cost and increased patient compliance which are sometimes as important contributors to chemotherapy failure as resistance, toxicity and lack of efficacy. One of the most important problems with conventional cytotoxic chemotherapeutic agents is dose limiting toxicities. These single agents should avoid these toxicities as they do not need to be as potent as conventional chemotherapeutic agents.

Compounds 1 and 2, Section D., (see FIG. 4, bottom row, far right column) each inhibit VEGFR-2 and PDGFR-β for antiangiogenic effects and also inhibit human TS (hTS) for cytotoxic effects in single agents.[12] The inhibitory potency of both these single agents against VEGFR-2, PDGFR-β, and hTS was better than or close to standards (Tables 9, 10). In a COLO-205 xenograft mouse model, one of the analogs significantly decreased tumor growth (tumor growth inhibition (TGI)=76% at 35 mg/kg), liver metastases, and tumor blood vessels compared with a standard drug and with control and thus demonstrated potent tumor growth inhibition, inhibition of metastasis, and antiangiogenic effects in vivo. These compounds afford combination chemotherapeutic potential in single agents.

TABLE 9

IC$_{50}$ values (μM) of kinase inhibition and A431 cytotoxicity[12] compounds 1-2, Section D.

| Compd # | EGFR Kinase Inhibition | VEGFR-2 (Flk-1) Kinase Inhibition | VEGFR-1 (Flt-1) kinase Inhibition | PDGFR-β Kinase Inhibition | A431 Cytotoxicity |
|---|---|---|---|---|---|
| 1 | 15.07 ± 3.1 | 22.6 ± 4.5 | 118.1 ± 19.4 | 2.8 ± 0.42 | 49.2 ± 4.7 |
| 2 | 10.41 ± 1.2 | 56.3 ± 7.1 | 160.1 ± 28.9 | 40.3 ± 5.1 | 14.1 ± 2.0 |
| PD153035 | 0.23 ± 0.05 | | | | |
| SU5416 | | 12.9 ± 2.9 | | | |
| CB67645 | | | 14.1 ± 2.8 | | |
| DMBI | | | | 3.75 ± 0.31 | |
| Cisplatin | | | | | 10.6 ± 3.5 |

TABLE 10

IC$_{50}$ Values (μM) of Thymidylate Synthase Inhibition[12] compounds 1-2, Section D.

| Compd # | Human | E. coli | Toxoplasma gondii |
|---|---|---|---|
| 1 | 0.54 | >27 | 0.11 |
| 2 | 0.39 | >26 | >26 |
| Pemetrexed | 29.0 | 15 | 14 |
| Raltitrexed | 0.29 | 2.3 | 0.48 |

The present invention provides the compounds of the following formula:

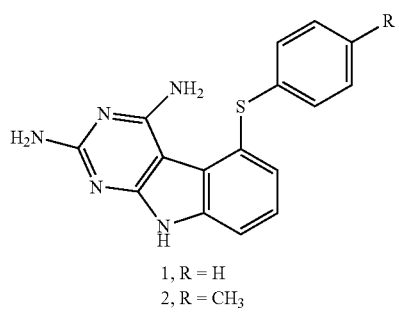

1, R = H
2, R = CH$_3$

3, R = H
4, R = CH₃

5

Lead compounds 1 and 2, Section D., showed good activity against VEGFR-2 and PDGFR-β in in-cell kinase assays (Table 9). Compounds 1 and 2, Section D., have a sulfur atom as a linker for 5-position substitution. From molecular modeling of the lead compounds 1 and 2, section D., we observed that the 5-position phenyl ring is surrounded by hydrophobic amino acid residues in VEGFR-2, PDGFR-β and hTS binding sites (not shown). Thus we designed isomers of compounds 1 and 2 with carbon (compounds 3 and 4, Section D.) and oxygen (compound 5, Section D.) atom linkers in place of the sulfur atom. With the use of calculations using MOE 2013.08)[13], these modifications result in changes in the dihedral angle and bond lengths of the linker region, which could alter the orientation of the 5-aryl moiety relative to the tricyclic scaffold. This could provide improved interactions with hydrophobic residues in the binding site of the targeted kinases and hTS and could result in increased potency and/or selectivity against RTKs and/or hTS. Docking studies of compounds 2 and 5, Section D. (not shown) having a stereoview, superimposition of docked poses of compound 2 and compound 5 in the ATP binding site of VEGFR-2 (PDB: 1YWN)[14], and stereoview, superimposition of docked poses of compounds 2 and 5, Section D. in the hTS crystal structure were carried out. (PDB: 1JU6)[14]

Molecular modeling studies were carried out for compounds 3-5 using crystal structures of VEGFR2 (PDB: 1YWN) and hTS (PDB: 1JU6) using LeadIT 2.1.3. The docking poses were visualized using CCP4MG.[14] The docked structure of compound 5 retains interactions at VEGFR-2 binding site predicted for the lead compound 2. Both compounds 2 and 5 show hydrogen bonds with Hinge region amino acids (4-NH₂ group with Glu915 (C=O); N3 with Cys917 (N—H) and 2NH₂ with Cys917 (C=O)). The 5-phenoxy ring fits in hydrophobic pocket 1 and interacts with Val897, Leu1033 and Cys1043. As expected, docking studies predict variations in the orientation of the 5-phenoxy ring of compound 5 compared to the corresponding thio-phenyl ring of compound 2 due to the altered heteroatom linker.

Compound 5, Section D., was predicted (score: −22.84 kJ/mol) to retain the activity of compound 2 (score: −20.66 kJ/mol) against VEGFR-2. Docking studies for compounds 2 and 5 in hTS show hydrogen bonds between the 2-NH₂ group and the side chain OH of Tyr258, 4NH₂ group and Asp218, and between the pyrrole NH and the backbone carbonyl of Ala111. Docking also reveals that the C-ring of both compounds show hydrophobic interactions with Trp109. In addition, the 5-phenoxy ring makes hydrophobic interactions with Ile108, Leu221, and Phe225 and is involved in stacking interactions with dUMP in the binding site. Docking studies suggest that compound 5 should be a potent inhibitor of hTS, similar to lead compound 2. Compounds 3 and 4 display similar docked poses in the targeted kinases and in hTS (not shown). Therefore, these compounds are predicted to be potent single agents with multiple RTK and hTS inhibitory activities.

Chemistry of Compounds of Section D.

Scheme 1D

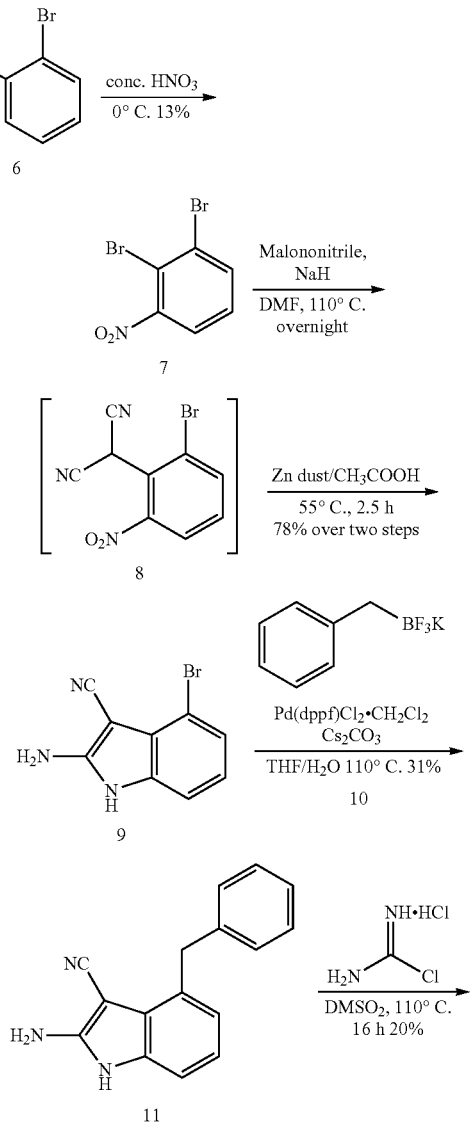

Scheme 3D

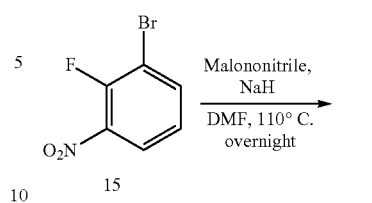

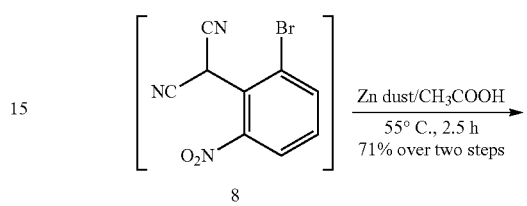

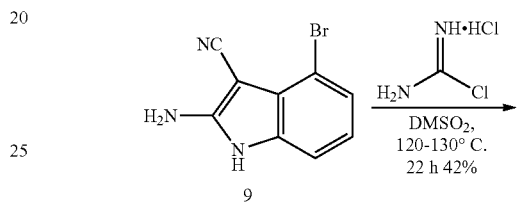

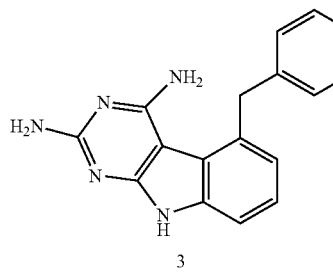

Scheme 2D

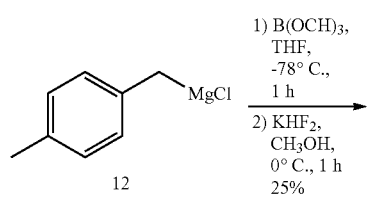

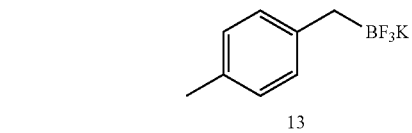

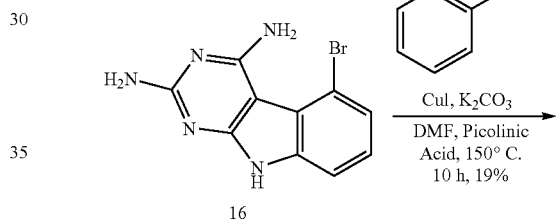

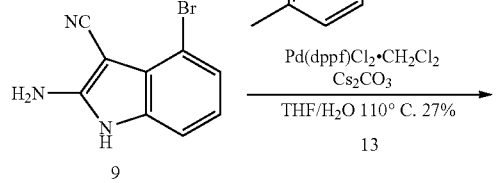

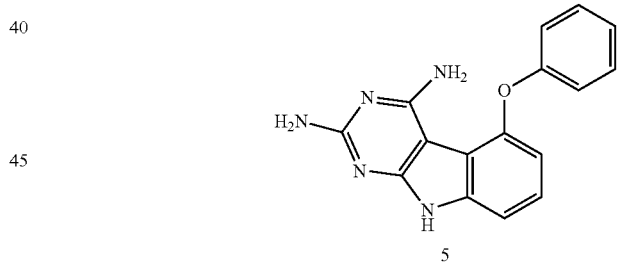

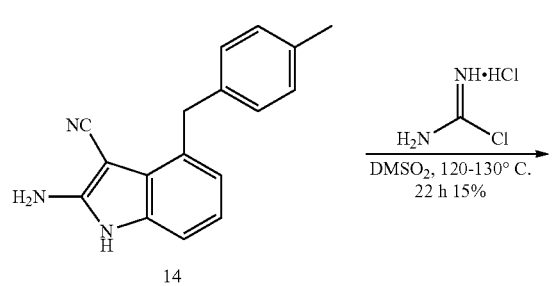

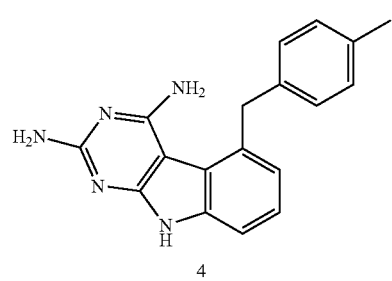

Suzuki coupling reactions between different trifluoroborate salts (compounds 10 and 13) (Scheme 1D and 2D) with common intermediate 2-amino-3-cyano-4-bromo indole (compound 9, Section D.) afforded compounds 11 and 14 in 31% and 27% yield, respectively. Subsequent cyclization of compounds 11 and 14 with carbamimidic chloride hydrochloride in DMSO$_2$ at 110° C. gave target compounds 3 and 4 in 20% and 15% yield, respectively. Trifluoroborate salt (compound 10) was commercially available whereas compound 13 was synthesized using a reported procedure.[15] Ullmann type coupling of sodium phenoxide with 5-bromo-9H-pyrimido[4,5-b]indole-2,4-diamine (compound 16) (Scheme 3D) afforded target compound 5, Section D., in 19% yield. Intermediate compound 9 was prepared by a similar synthetic method as described in Scheme 1D starting with 2-fluoro-3-bromo nitrobenzene (compound 15) which gave compound 9 in 71% overall yield. Cyclization with carbamimidic chloride hydrochloride in DMSO$_2$ at 110° C. gave intermediate compound 16 in 42% yield.

SECTION D. REFERENCES

1) Chu, E.; Callender, M. A.; Farrell, M. P.; Schmitz, J. C. Cancer Chemother. Pharmacol. 2003, 80, 897.
2) Danenberg, P. V. Biochim. Biophys. Acta 1977, 47, 73-92.
3) Pizzorno, G. D., R. B.; Cheng, Y-C. Pyrimidine and Purine Antimetabolites, in Cancer Medicine, J. F. Holland and E. Frei III, Eds. B. C. Decker, Inc., Hamilton, London. 2003, 739-744.
4) Taylor, E. C.; Kuhnt, D.; Shih, C.; Rinzel, S. M.; Grindey, G. B.; Barredo, J.; Jannatipour, M.; Moran, R. J. Med. Chem. 1992, 35, 4450-4454.
5) Jackman, A. L.; Taylor, G. A.; Gibson, W.; Kimbell, R.; Brown, M.; Calvert, A. H.; Judson, I. R.; Hughes, L. R. Cancer Res. 1991, 51, 5579-5586.
6) Carmeliet, P. Nat. Med. 2003, 9, 653.
7) Herbst, R. S.; Johnson, D. H.; Mininberg, E.; Carbone, D. P.; Henderson, T.; Kim, E. S.; Blumenschein, G., Jr.; Lee, J. J.; Liu, D. D.; Truong, M. T.; Hong, W. K.; Tran, H.; Tsao, A.; Xie, D.; Ramies, D. A.; Mass, R.; Seshagiri, S.; Eberhard, D. A.; Kelley, S. K.; Sandler, A. J. Clin. Oncol. 2005, 23, 2544.
8) Hammerman, P. S.; Janneand, P. A.; Johnson, B. E. Clin. Cancer Res. 2009, 15, 7502.
9) Wilhelm, S. M.; Carter, C.; Tang, L.; Wilkie, D.; McNabola, A.; Rong, H.; Chen, C.; Zhang, X.; Vincent, P.; McHugh, M.; Cao, Y.; Shujath, J.; Gawlak, S.; Eveleigh, D.; Rowley, B.; Liu, L.; Adnane, L.; Lynch, M.; Auclair, D.; Taylor, I.; Gedrich, R.; Voznesensky, A.; Riedl, B.; Post, L. E.; Bollag, G.; Trail, P. A. Cancer Res. 2004, 64, 7099.
10) Mandel, D. B.; Laird, A. D.; Xin, X.; Louie, S. G.; Christensen, J. G.; Li, G.; Schreck, R. E.; Abrams, T. J.; Ngai, T. J.; Lee, L. B.; Murray, L. J.; Carver, J.; Chan, E.; Moss, K. G.; Haznedar, J. O.; Sukbuntherng, J.; Blake, R. A.; Sun, L.; Tang, C.; Miller, T.; Shirazian, S.; McMahon, G.; Cherrington, J. M. Clin. Cancer Res. 2003, 9, 327.
11) Klement, G.; Baruchel, S.; Rak, J.; Man, S.; Clark, K.; Hicklin, D. J.; Bohlen, P.; Kerbel, R. S. J. Clin. Investig. 2000, 105, R15-R24.
12) Gangjee, A.; Zaware, N.; Raghavan, S.; Ihnat, M.; Shenoy, S.; Kisliuk, R. L. J. Med. Chem. 2010, 53, 1563-1578.
13) Molecular Operating Environment (MOE 2011.10), Chemical Computing Group, Inc., 1255 University Street, Suite 1600, Montreal, Quebec, Canada, H3B 3X3. www.chemcomp.com
14) McNicholas, S.; Potterton, E.; Wison, K. S.; Noble, E. M. Acta Cryst. 2011, D67, 386-394.
15) Molander, G. A.; Petrillo, D. E. Org. Synth. 2007, 84, 317-324.

SECTION E

Design, Synthesis and Biological Evaluation of Substituted Monocyclic Pyrimidines with Cytotoxic and Antitubulin Activities as Antitumor Agents Cellular microtubules are dynamic filamentous polymers composed of α and β-tubulin heterodimers, and they play a key role in cell mitosis by forming the mitotic spindle. Microtubule inhibitors disrupt or suppress both the microtubule structure and its normal functions by inhibition or promotion of microtubule assembly, resulting in cell cycle arrest in the mitotic phase and induction of apoptosis.[1] An overly simplistic classification of antimitotics includes microtubule-stabilizing or polymerizing agents (exemplified by taxanes) and microtubule destabilizing agents (exemplified by the vinca alkaloids).[2] Taxanes bind to the interior of the microtubule on the β-subunits. In contrast, the vinca alkaloids also bind tubulin but at a site distinct from that of taxoids. Recently, a prodrug (combretastatin A-4 phosphate, CA4P) of the potent colchicine site compound combretastatin A-4 (CA4) has been approved for clinical trials.[3] The colchicine site is primarily on β-tubulin, but at its interface with the α-subunit of the same tubulin heterodimer. Interfering with microtubule polymerization has been a viable strategy for the development of highly successful antitumor drug classes. FIG. 1 show the structures of microtubule-targeting agents.

Multidrug resistance (MDR) is a major limitation of clinically used antimitotic agents, and MDR tumors are usually resistant to microtubule disrupting agents. Overexpression of P-glycoprotein (Pgp) has been reported in the clinical setting in several tumor types, particularly after patients have received chemotherapy.[4] Moreover, Pgp expression may act as a prognostic indicator in certain cancers and is associated with poor response to chemotherapy by inducing resistance in the presence of cytotoxic drugs.[5] Another clinical mechanism of resistance to tubulin-binding drugs is the overexpression of specific isotypes of β-tubulin, particularly βIII-tubulin. The overexpression of βIII-tubulin in multiple tumor types, including breast, ovarian and non-small cell lung cancers,[6] is involved in resistance to taxanes and vinca alkaloids.

SECTION E. COMPOUNDS

The present invention provides the following compounds:

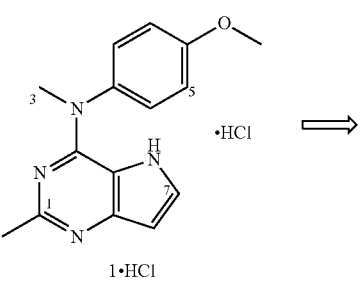

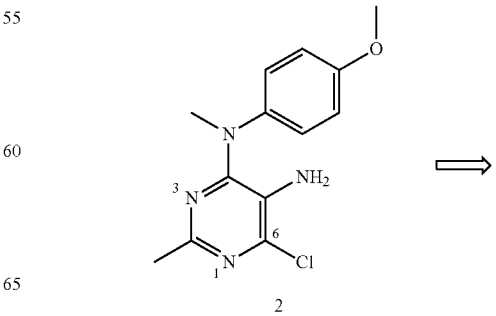

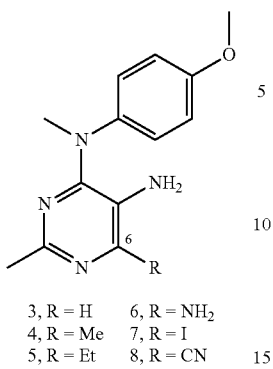

3, R = H   6, R = NH₂
4, R = Me  7, R = I
5, R = Et  8, R = CN

This invention provides lead compound 2 and target compounds 3-8, Section E.

Recently, Gangjee et al.[7] reported a novel compound 1.HCl (Section E, structure shown above) that inhibits tubulin assembly and affords cytotoxic effects. Compound 2, Section E, structure shown above) an open chain conformationally flexible analog of compound 1.HCl, was designed and found to be 5-times more potent against tubulin polymerization as compared with the lead compound 1.HCl.[8] This finding prompted a SAR study and this report addresses the effect of removal of the 6-Cl moiety of compound 2 (see compound 3, Section E, structure shown above) and substitution of the 6-Cl moiety of compound 2 with electron donating (compounds 4-6, Section E, structures shown above) and electron withdrawing groups (compounds 7=8, Section E., structures shown above) on biological activity.

Chemistry of Compounds of Section E.

Scheme 1E

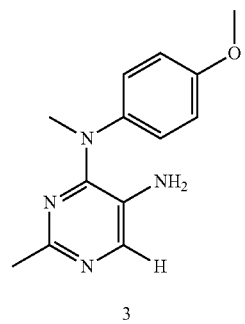

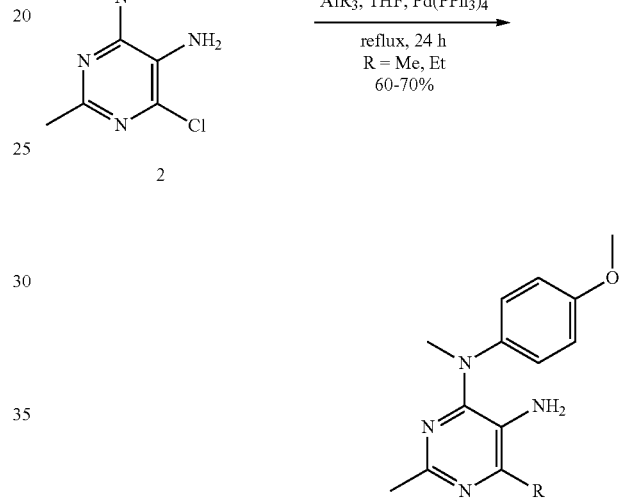

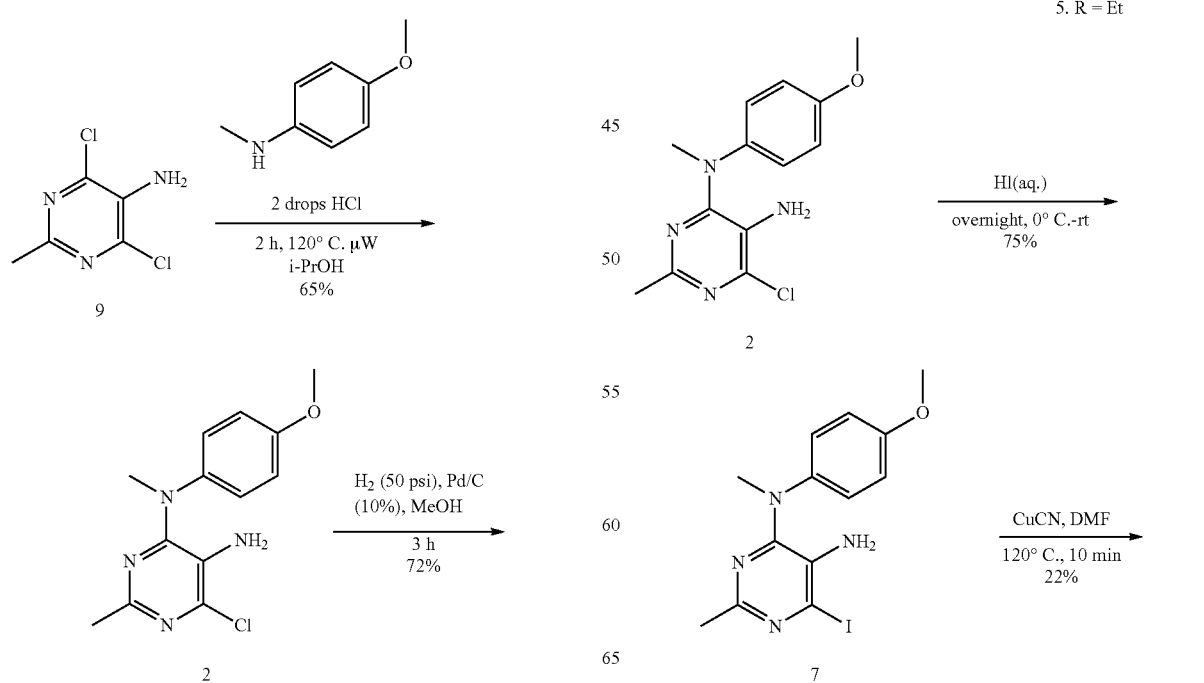

Biological Data for Compounds of Section E.

TABLE 11

| Compd. | Inhibition of tubulin assembly $IC_{50} \pm SD$ (μM) |
|---|---|
| CA4 | 0.96 ± 0.07 |
| 1.HCl | 10 ± 0.6 |
| 2 | 2.1 ± 0.04 |
| 3 | 11 ± 0 |
| 4 | 18 ± 2 |
| 5 | >20 |
| 6 | >20 |
| 7 | 3.4 ± 0.07 |
| 8 | >20 (partial activity) |

Table 11 shows that the removal of the 6-chloro (compound 3, section E.) led to a 5.5-fold decrease in potency as an inhibitor of tubulin polymerization. Replacement of the chloro with lipophilic electron donating groups (compounds 4 and 5, section E.) led to a further decrease in activity. Compound 5, Section E., with an ethyl at the 6-position was inactive. Compound 6, Section E., with a $NH_2$ at the 6-position was also inactive. Substitution of the 6-chloro with an iodo moeity (compound 7, Section E.) was tolerated, albeit with a 1.5-fold reduction in potency. Compound 8, Section E., with a hydrophilic electron withdrawing nitrile group at the 6-position had partial activity. Thus, a lipophilic electron withdrawing group at the 6-position appears to be necessary for activity.

TABLE 12

Compounds 2, 5, and 7, Section E., Circumvent Pgp Mediated Resistance

| | Effect of Pgp on drug sensitivity[a] $IC_{50} \pm SD$ (nM) | | |
|---|---|---|---|
| Compd. | Parental OVCAR-8 | Pgp Overexpressing NCI/ADR-RES | Rr[b] |
| paclitaxel | 10.0 ± 0 | 5,000 ± 0 | 500 |
| CA4 | 6 ± 0.7 | 9.0 ± 2 | 1.5 |
| 2 | 25 ± 5 | 20 ± 0 | 0.8 |
| 5 | 2200 ± 500 | 610 ± 20 | 0.27 |
| 7 | 450 ± 70 | 250 ± 70 | 0.56 |

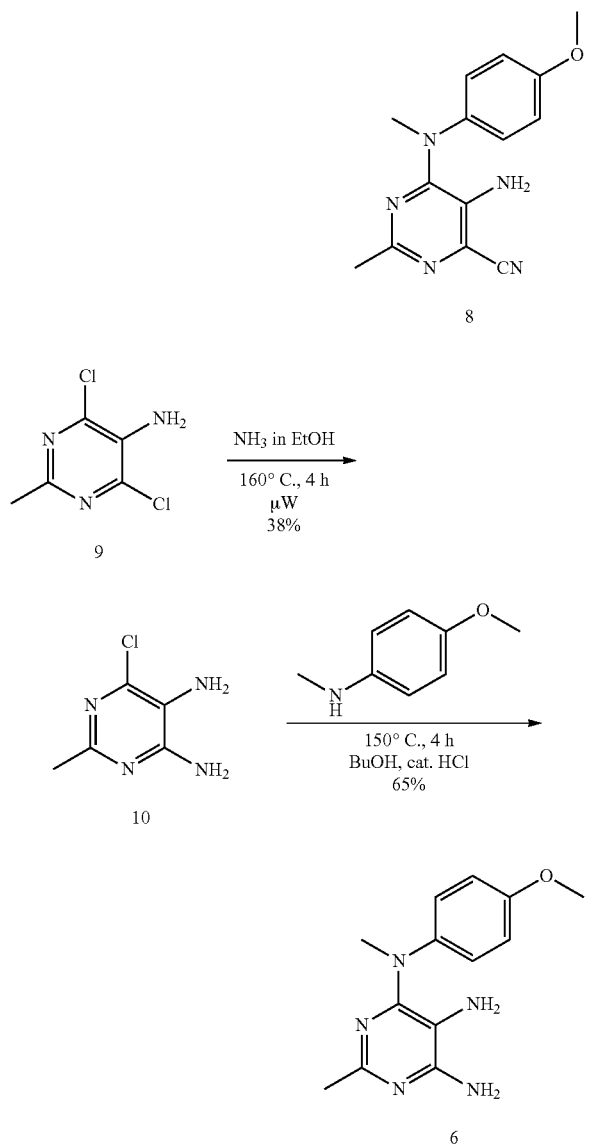

Dichloropyrimidine (compound 9, Scheme 1E) was subjected to nucleophilic displacement with 4-methoxy-N-methylaniline and a catalytic amount of concentrated HCl in the presence of i-PrOH to afford compound 2, Section E. Compound 2, section E., was hydrogenated under Pd/C at 50 psi for 3 hours (h) to afford compound 3, Section E. The synthesis of compounds 4 and 5, Section E., used trialkyl-aluminium in the presence of Pd catalyst and THF under reflux conditions. Compound 7, Section E., was obtained from 2 using aqueous hydriodic acid at 0° C.-rt. Compound 7 was then heated at 120° C. in the presence of DMF and copper cyanide to yield compound 8, Section E. One of the chloro groups of compound 9, Section E, was substituted with the amino group under $S_NAr$ conditions with ethanolic ammonia to produce compound 10, Section E., which was then subjected to nucleophilic displacement with 4-methoxy-N-methylaniline and a catalytic amount of concentrated HCl in the presence of butanol to afford compound 6, Section E.

TABLE 13

Compounds 3 and 4, Section E., Circumvent βIII-Tubulin Resistance

| | Effect of βIII on drug sensitivity[a] $IC_{50} \pm SD$ (nM) | | |
|---|---|---|---|
| Compd. | Wild type HeLa | βIII Overexpressing HeLa | Rr[b] |
| paclitaxel | 5.3 ± 2 | 16 ± 1 | 3.01 |
| CA4 | 1.8 ± 0.4 | 2.5 ± 0.7 | 1.38 |
| 3 | 1700 ± 500 | 2500 ± 0 | 1.47 |
| 4 | 1600 ± 300 | 2500 ± 0 | 1.56 |

[a]Antiproliferative effects of compounds 2-5, 7, Section E., in parental and MDR-1 cell lines in comparison with other microtubule disrupting agents. The $IC_{50}$ values were determined using the SRB assay (n = 3 (SD).
[b]Rr: Relative resistance. The Rr was calculated by dividing the $IC_{50}$ of the Pgp or β-III overexpressing cell line by the $IC_{50}$ of the parental cell line.

The ability of compounds 5 and 7, Section E., to circumvent Pgp-mediated drug resistance was evaluated using an OVCAR-8 isogenic cell line pair (Table 12). In this cell line pair, the relative resistance (Rr) of paclitaxel is 500 while Rr values of less than 1 were obtained with compounds 5 and 7, Section E., consistent with the Rr value obtained with CA4 of 1.5. Remarkably, compounds 5 and 7, Section E., are 1.8-3.6-fold more potent in the Pgp overexpressing cell as compared with the parental line, indicating a possible utility against paclitaxel resistant ovarian cancer. These data suggest that compounds 2, 5, and 7, Section E., are poor substrates for transport by Pgp and thus have advantages over some clinically useful tubulin-targeting drugs like paclitaxel. A HeLa cell line pair was used to study the effects of βIII tubulin on the potency of compounds 3 and 4, Section E. (Table 13). The WT βIII cell line was generated from HeLa cells transfected with the gene for βIII-tubulin. Compounds 3 and 4 have Rr values from 1.47-1.56, suggesting that these compounds overcome drug resistance mediated by βIII-tubulin as compared with paclitaxel, which has a Rr of 3.01 in these cell lines. Thus compounds 2-5, and 7, Section E., inhibit the proliferation of human cancer cells without regard to their expression of Pgp or βIII-tubulin.

It will be appreciated by those persons skilled in the art that this invention provides for the synthesis and evaluation of compounds 2-8, Section E., as tubulin inhibitors and as antitumor agents. It was found that the chloro group (or other lipophilic electron withdrawing groups like iodo) at the 6-position is required for activity against tubulin polymerization. In addition, compounds 2, 5, and 7, Section E., displayed better potency in a Pgp overexpressing tumor cell line as compared with its isogenic control, indicating that these analogs perhaps antagonize Pgp. Compounds 3 and 4, Section E., overcame resistance mediated by βIII-tubulin.

SECTION E. REFERENCES

1. Dumontet, C.; Jordan, M. A. Microtubule-binding agents: A dynamic field of cancer therapeutics. *Nat. Rev. Drug Discov.* 2010, 9, 790-803.
2. Jordan, M. A.; Kamath, K. How do Microtubule-targeted drugs work? An overview. *Curr. Cancer Drug Targets* 2007, 7, 730-742.
3. Massarotti, A.; Coluccia, A.; Silvestri, R.; Sorba, G.; Brancale, A. The Tubulin Colchicine Domain: a Molecular Modeling Perspective. *Chem Med Chem.* 2012, 7, 33-42.
4. Fojo, A. T.; Menefee, M. Microtubule targeting agents: Basic mechanisms of multidrug resistance (MDR). *Semin. Oncol.* 2005, 32, S3-S8
5. McCarroll, J. A.; Gan, P. P.; Liu, M.; Kavallaris, M. βIII-Tubulin is a multifunctional protein involved in drug sensitivity and tumorigenesis in non-small cell lung cancer. *Cancer Res.* 2010, 70, 4995-5003.
6. Chiou, J. F.; Liang, J. A.; Hsu, W. H.; Wang, J. J.; Ho, S. T.; Kao, A. Comparing the relationship of taxol-based chemotherapy response with P-glycoprotein and lung resistance-related protein expression in non-small cell lung cancer. *Lung* 2003, 181, 267-273.
7. Gangjee, A.; Pavana, R. K.; Li, W.; Hamel, E.; Westbrook, C.; Mooberry, S. L. Novel water-soluble substituted pyrrolo[3,2-d]pyrimidines: design, synthesis and biological evaluation as antitubulin antitumor agents. *Pharm. Res.* 2012, 29, 3033-3039.
8. Gangjee, A.; Mohan R.; Bai R.; Hamel, E.; Ihnat M. From Abstracts of Papers, 246th American Chemical Society National Meeting and Exposition (ACS), Indianapolis, Ind., Sep. 8-12, 2011. Abstract No: 311.

It will be appreciated by those persons skilled in the art that changes could be made to the embodiments described above without departing from the broad inventive concept thereof. It is understood therefore, that this invention is not limited to the particular embodiments disclosed, but it is intended to cover modifications that are within the spirit and scope of the invention, as defined by the appended claims.

What is claimed is:
1. A compound of the formula:

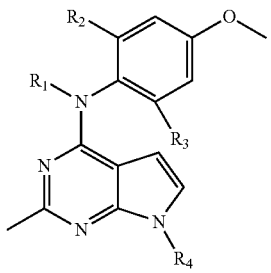

wherein $R_1$ is a methyl group, $R_2$ is hydrogen, $R_3$ is hydrogen, and $R_4$ is an alkyl group having from three to five carbon atoms, or a pharmaceutically acceptable salt or hydrate thereof.

2. A pharmaceutical composition comprising a therapeutically effective amount of a compound of the formula:

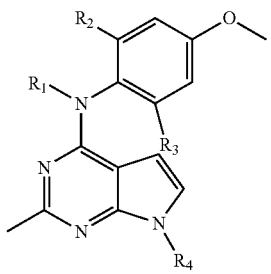

wherein $R_1$ is a methyl group, $R_2$ is hydrogen, $R_3$ is hydrogen, and $R_4$ is an alkyl group having from three to five carbon atoms, or a pharmaceutically acceptable salt or hydrate thereof.

* * * * *